United States Patent
Wang et al.

(10) Patent No.: US 9,447,015 B1
(45) Date of Patent: Sep. 20, 2016

(54) (S)-2'-VINYL-ABSCISIC ACID DERIVATIVES

(71) Applicant: Valent BioSciences Corporation, Libertyville, IL (US)

(72) Inventors: Gary T. Wang, Libertyville, IL (US); Daniel F. Heiman, Libertyville, IL (US); Gregory D. Venburg, Deerfield, IL (US); Joseph Lustig, Lake Barrington, IL (US); Marci Ann Surpin, Highland Park, IL (US); Robert Erwin Fritts, Jr., Clovis, CA (US); Franklin Paul Silverman, Highland Park, IL (US); Derek D. Woolard, Zion, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

(21) Appl. No.: 15/099,697

(22) Filed: Apr. 15, 2016

Related U.S. Application Data

(60) Provisional application No. 62/147,869, filed on Apr. 15, 2015.

(51) Int. Cl.
*C07C 59/90* (2006.01)
*C07D 307/54* (2006.01)
*C07D 277/30* (2006.01)
*C07D 213/55* (2006.01)

(52) U.S. Cl.
CPC .............. *C07C 59/90* (2013.01); *C07D 213/55* (2013.01); *C07D 277/30* (2013.01); *C07D 307/54* (2013.01)

(58) Field of Classification Search
CPC .. C07C 59/90; C07D 307/54; C07D 277/30; C07D 213/55
See application file for complete search history.

(56) References Cited

PUBLICATIONS

Rose et al. Bioorg. Med. Chem. Lett. 1997, 7, 2543-2546.*

* cited by examiner

*Primary Examiner* — Matthew Coughlin
(74) *Attorney, Agent, or Firm* — Wood, Phillips, Katz, Clark & Mortimer

(57) ABSTRACT

The invention relates to a novel class of (S)-2'-vinyl-substituted-abscisic acid derivatives, and to methods of synthesizing and using the derivatives.

30 Claims, No Drawings

(S)-2'-VINYL-ABSCISIC ACID DERIVATIVES

FIELD OF THE INVENTION

The present invention is directed to a novel class of derivatives of (S)-abscisic acid ("(S)-ABA") and methods of synthesizing the same.

BACKGROUND OF THE INVENTION

Abscisic Acid ("ABA") is a naturally occurring plant growth regulator that regulates a wide range of plant physiological processes such as seed germination, seedling elongation, abiotic stress response, flowering, and fruit development. The naturally occurring and most biologically active form of ABA is the S enantiomer (S)-ABA. Consequently, a variety of commercial utilities have been identified for (S)-ABA in horticulture and agronomy. (S)-ABA exerts its biological activities by binding to (S)-ABA receptors and activating cellular signal transduction cascades. In addition, (S)-ABA has been demonstrated to have pharmaceutical and nutraceutical utilities (see U.S. Pat. No. 8,536,224).

Synthetic derivatives of ABA may exhibit biological activities either similar to (S)-ABA but with altered (enhanced) potency (ABA agonists) or with a differing spectrum of affinity for the multiple ABA receptors than (S)-ABA itself. Conversely, synthetic derivatives may act biologically in opposition to (S)-ABA (i.e. as ABA antagonists). The synthetic derivatives may also possess improved uptake by plant tissues as well as enhanced metabolic stability. Additionally, synthetic derivatives may have better chemical and environmental stability than (S)-ABA. Thus, synthetic ABA derivatives may possess unique biological activities and have been pursued as an approach to identify novel plant growth regulators.

A variety of synthetic derivatives of ABA have been known in the public domain. Several Japanese research groups have synthesized ABA derivatives with modifications of the side chain and/or with cyclohexenone ring substituents through de novo synthesis (Y. Todoroki, at al., *Phytochem.* 1995, 38, 561-568; Y. Todoroki, et al., *Phytochem.* 1995, 40, 633-641; S. Nakano, et al., *Biosci. Biotech. Biochem.* 1995, 59, 1699-176; Y. Todoroki, et al., *Biosci. Biotech. Biochem.* 1994, 58, 707-715; Y. Todoroki, et al., *Biosci. Biotech. Biochem.* 1997, 61, 2043-2045; Y. Todoroki, et al., *Tetrahedron,* 1996, 52, 8081-8098). Synthesis of (S)-3'-halogen-ABA, (S)-3'-azido-ABA and (S)-alkylthio-ABA from (S)-ABA have also been reported (Y. Todoroki, et al., *Tetrahedron,* 1995, 51, 6911-6926; S. Arai, et al., *Phytochem.* 1999, 52, 1185-1193; J. J. Balsevich, et al., *Phytochem.* 1977, 44, 215-220; Y. Todoroki, et al. *Tetrahedron,* 2000, 56, 1649-1653; Y. Todoroki, et al., *Bioorg. Med. Chem. Lett.* 2001, 11, 2381-2384). The work done by S. R. Abrams and coworkers at the Plant Biotechnology Institute at National Research Council of Canada is also noteworthy. Using de novo synthesis approaches, ABA derivatives with modified side-chains or $C_6'$-substitution have been prepared either as racemic mixtures or, in some cases, as pure stereoisomers (see U.S. Pat. No. 5,518,995; D. M. Priest, et al., *FEBS Letters,* 2005, 579, 4454-4458). A tetralone series of derivatives in which the cyclohexenone ring of (S)-ABA is replaced with a bicyclic tetralone ring has also been described (J. M. Nyangulu, et al., *Org. Biomol. Chem.* 2006, 4, 1400-1412; J. M. Nyangulu, et al., *J. Am. Chem. Soc.* 2005, 127, 1662-1664; WO2005/108345).

A few of the examples of (S)-ABA synthetic derivatives prepared in the literature are reported to have biological activity as ABA antagonists. A recent example is the work reported by Takeuchi where a series of (S)-3'-alkylsulfanyl-ABA derivatives were made and tested (Takeuchi, et al., *Nature Chem. Biol.* 2014, 10, 477-482).

The synthetic ABA derivatives reported in the literature thus far are limited in scope and are typically prepared via multi-step de novo synthesis. The syntheses generally suffer from low overall yields, particularly when the optically pure single enantiomers are desired. Thus, these compounds are generally expensive to synthesize in large quantities or to manufacture on a commercial scale, limiting their commercial application. The (S)-ABA derivatives of the present invention possess the aforementioned biological activities and, more importantly, can be prepared efficiently in single-enantiomer form from (S)-ABA, which until recently was not available in large quantities.

Accordingly, there is a need for enantiomerically pure (S)-ABA derivatives which are agonists and/or antagonists of (S)-ABA with improved or oppositional biological activity, respectively. There is also a need for improved (S)-ABA derivative synthesis methods.

SUMMARY OF THE INVENTION

In one aspect, the invention is directed to single enantiomer compounds of Formula I:

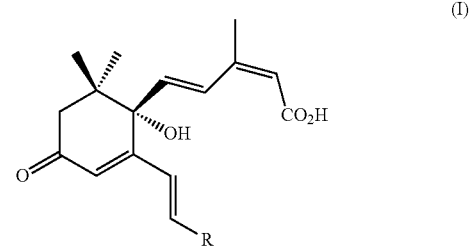

(I)

wherein R is selected from the group consisting of a substituted or unsubstituted benzene, naphthylene, monocyclic or bicyclic heterocyclic aromatic ring, and salts thereof.

In another aspect, the invention is directed to a process for making the compounds of the present invention.

In a further aspect, the invention is directed to methods for regulating plant growth comprising applying an effective amount of at least one of the compounds of the present invention to a plant in need of growth regulation.

DETAILED DESCRIPTION OF THE INVENTION

Applicant has discovered new (S)-ABA derivatives which are enantiomerically pure and methods for synthesizing these (S)-ABA derivatives. The compounds of the present invention are (S)-ABA derivatives that are relatively easy to synthesize.

In one embodiment, the present invention is directed to enantiomerically pure compounds of Formula I:

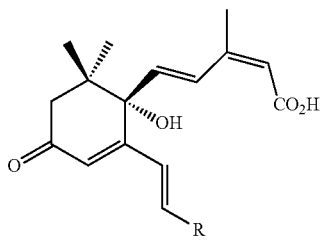

(I)

wherein R is selected from the group consisting of a substituted or unsubstituted benzene, naphthylene, a monocyclic or bicyclic heterocyclic aromatic ring, and salts thereof.

In an embodiment, R is unsubstituted benzene.

In a preferred embodiment, R is a substituted benzene.

In a more preferred embodiment, the benzene ring can be mono-, di-, tri-, tetra- or penta-substituted.

In another embodiment, the benzene ring substitution is selected from the group consisting of halogen, substituted or unsubstituted alkyl, cyano, alkoxy, nitro, sulfonyl, carbonyl, carboalkoxy and carbamoyl.

In a preferred embodiment, the benzene ring substitution is an unsubstituted lower alkyl. In a more preferred embodiment, the unsubstituted lower alkyl is methyl. In a most preferred embodiment, the methyl substitution is 4-methyl-.

In yet another embodiment, the benzene ring is mono-substituted with one halogen. In a more preferred embodiment, the halogen is fluorine or chlorine.

In a further preferred embodiment, the benzene ring halogen substitution is 4-chloro.

In a further embodiment, the benzene ring is disubstituted with two halogen substitutions, including difluoro-, dichloro-, and chloro-fluoro-.

In a further preferred embodiment, the benzene ring dihalogen substitutions are 3-chloro-4-fluoro-.

In an alternative preferred embodiment, the benzene ring dihalogen substitutions are 3,4-difluoro.

In yet another embodiment, the benzene ring is mono-substituted with dihalomethyl or trihalomethyl. In a preferred embodiment, the benzene ring substitution is trihalomethyl. In a more preferred embodiment, the trihalomethyl is trichloromethyl or trifluoromethyl. In a most preferred embodiment, the benzene ring substitution is 4-trifluoromethyl.

In another embodiment, the benzene ring is disubstituted with at least one halogen and at least one dihalomethyl or trihalomethyl. In a preferred embodiment, the benzene ring substitutions are a halogen and a trihalomethyl. In a more preferred embodiment, the halogen is fluoro and the trihalomethyl is trifluoromethyl. In a most preferred embodiment the fluoro is 2-fluoro and the trifluoromethyl is 3-trifluoromethyl.

In another embodiment, R is a mono-cyclic or bicyclic heterocyclic aromatic ring.

In a preferred embodiment, the heterocyclic aromatic ring is selected from the group consisting of pyridine, furan, thiazole, and salts thereof.

In a more preferred embodiment, R is a pyridyl group. In a further preferred embodiment, the pyridyl is selected from the group consisting of 2-pyridyl, 3-pyridyl and 4-pyridyl.

In another embodiment, R is a furyl group. In a further preferred embodiment, the furyl group is a 2-furyl group.

In yet another preferred embodiment, R is a thiazolyl group. In a further preferred embodiment, the thiazolyl is selected from the group consisting of 2-thiazolyl and 3-thiazolyl.

In an alternative embodiment, the present invention is directed to a process for making the compounds of Formula I. This process includes (Step a) reacting (S)-abscisic acid with an alkylating agent R'X and a base in a solvent, (Step b) treating the compound resulting from Step a with a base and an aryl or heteroaryl aldehyde in a solvent, and (Step c) treating the compound resulting from Step b with a base, water and an organic solvent. This synthesis is illustrated in Scheme I below.

Scheme I:

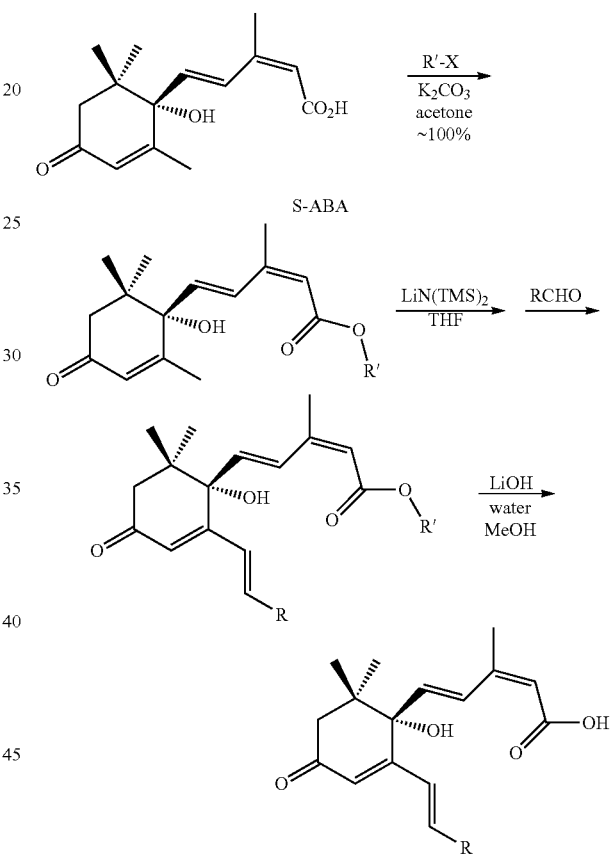

Suitable alkylating agents for use in Step a include methyl iodide and methyl sulfate (R'=methyl), ethyl iodide, (R'=ethyl) and benzyl bromide (R'=benzyl).

Suitable bases for use in Step a include potassium carbonate, sodium carbonate, cesium carbonate, sodium hydroxide and potassium hydroxide.

Suitable solvents for use in Step a include acetone, N, N-dimethylformamide, N-methylpyrolidone and dimethylsulfoxide.

Suitable bases for use in Step b include lithium bis (trimethylsilyl)amide and sodium hydride.

Suitable solvents for use in Step a include tetrahydrofuran and N, N-dimethylformamide.

Suitable bases for use in Step c include lithium hydroxide, sodium hydroxide and potassium hydroxide.

Suitable organic solvents for use in Step c include methanol, ethanol and isopropanol.

In another embodiment, the present invention is directed to methods for regulating plant growth comprising applying an effective amount of at least one of the compounds of the present invention to a plant in need of growth regulation.

The compounds of the present invention have a wide range of utilities, including promoting germination in plant species with high seed dormancy, promoting and synchronizing bud break in woody perennial plant species, promoting plant growth, promoting plant heat stress tolerance, and inhibiting leaf yellowing, flower drop, and leaf drop in ornamental plant species. Additionally, these compounds may have utility in the nutraceutical and pharmaceutical areas.

The disclosed embodiments are simply exemplary embodiments of the inventive concepts disclosed herein and should not be considered as limiting, unless the claims expressly state otherwise.

DEFINITIONS OF TERMS

As used herein, "vinyl" refers to the functional group —CH=CH$_2$, which is an ethylene molecule (H$_2$C=CH$_2$) minus one hydrogen atom.

As used herein, "alkenyl" refers to the functional group —CR'=CR"R'", which is an substituted ethylene molecule (R'HC=CR'R'") minus one hydrogen atom.

As used herein, "alkyl" refers to a saturated straight or branched chain alkane radical (i.e. a group missing one of the hydrogen atoms that would be required for a stable molecule) and containing at least one carbon (—C$_n$H$_{2n+1}$). Examples of alkyls include methyl, ethyl, propyl, iso-propyl, butyl, sec-butyl, pentyl, hexyl, heptyl, octyl, nonyl, decyl, undecyl, and dodecyl. As used herein, "lower alkyl" refers to an alkyl with 6 or fewer carbons.

As used herein, "substituted alkyl" refers to a straight or branched chain alkane radical that contains at least one carbon and one of the hydrogens of the core structure has been replaced. Examples of substituted alkyls include hydroxymethyl (—CH$_2$OH), hydroxybutyl (—C$_4$H$_8$—OH), trifluoromethyl (—CF$_3$), pentafluoroethyl (—CF$_2$CF$_3$).

As used herein, "substituted compound" is one in which one or more hydrogen atoms of a core structure have been replaced with a functional group such as alkyl, hydroxy, or halogen.

As used herein, "substituted benzene ring" refers to a benzene ring wherein one or more hydrogen atoms of a core structure have been replaced with a functional group, such as an alkyl or a halogen.

As used herein, "pyridine" refers to a six-membered ring heterocyclic aromatic compound with the chemical formula C$_5$H$_5$N. It is structurally similar to benzene but it has one methine group (=CH—) replaced by a nitrogen atom.

As used herein, "furan" refers to a five membered heterocyclic aromatic compound with the chemical formula C$_4$H$_4$O.

As used herein, "thiazole" refers to five membered heterocyclic aromatic compound that contains a sulfur and a nitrogen atom.

As used herein, "cyano" refers to a radical with the formula —CN.

As used herein, "halo-" refers to fluoro-, chloro-, bromo- or iodo-. Embodiments of the present invention include di and trihalogens.

As used herein, "dihalomethyl" refers to a functional group with two halogens replacing the hydrogens of methyl. For example, —CHF$_2$.

As used herein, "trihalomethyl" refers to a functional group with three halogens replacing the hydrogens of methyl. For example, —CF$_3$.

As used herein, "enantiomerically pure" or "(S)" refer to the presence of a single enantiomer of ABA with the relative enantiomeric purity of greater than 95%.

As used herein, "racemic" or "(±)" refer to a relatively equal mixture of R/S enantiomers.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases, such as Na$^+$ or K$^+$ salts derived from neutralization of an ABA carboxylic acid group with sodium hydroxide or potassium hydroxide or R$_1$R$_2$R$_3$R$_4$N$^+$ salts prepared by neutralization with an amine. Amine salts include but are not limited to the ammonium salt prepared by neutralization with ammonium hydroxide or the triethylammonium salt prepared by neutralization with triethylamine.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

Example 1

Compound 1a

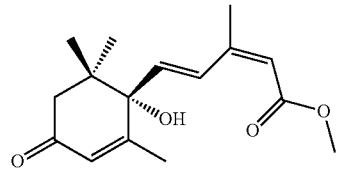

(2Z,4E)-methyl 5-((S)-1-hydroxy-2,6,6-trimethyl-4-oxocyclohex-2-en-1-yl)-3-methylpenta-2,4-dienoate A solution of (S)-ABA (53 g, 0.2 mole) in acetone (800 ml) was cooled with an ice bath. Cesium carbonate (98 g, 0.3 mole) was added. The mixture was stirred for ten minutes, then methyl iodide (24.8 ml, 56.5 g, 0.4 mole) was added. After stirring at ambient temperature overnight, the mixture was concentrated to ~300 ml and water (500 ml) was added. The resulting mixture was then extracted with ethyl acetate (3×200 ml). The resulting organic solution was washed twice with saturated aqueous sodium sulfite solution, dried (MgSO$_4$) and filtered. Evaporation of the filtrate gave the title compound as an off-white solid (56 g).

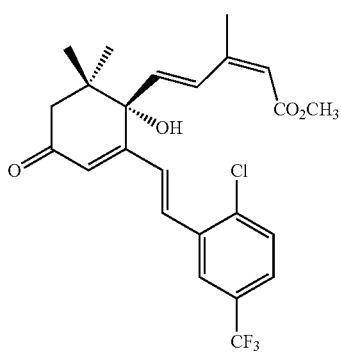

(2Z,4E)-methyl 5-((S)-2-((E)-2-chloro-5-
(trifluoromethyl)styryl)-1-hydroxy-6,6-
dimethyl-4-oxocyclohex-2-en-1-yl)-3-
methylpenta-2,4-dienoate A solution of Compound 1a (0.56 g, 2.0 mmole) in anhydrous tetrahydrofuran (THF, 10 mL) was cooled to 0° C. with an ice bath under an atmosphere of nitrogen. Lithium hexamethyl disilazane (1.0 M solution in THF, 3.0 mL) was added dropwise via a syringe over 10 minutes. The resulting solution was stirred at 0° C. for 30 minutes and the ice bath was removed. A solution of 2-chloro-5-trifluoromethylbenzaldehyde (2.08 g, 10 mmole) in anhydrous THF (4 mL) was then added via a syringe over 5 minutes. The resulting solution was stirred at ambient temperature overnight. The reaction was then quenched with water (20 mL) and acidified to ~pH 2.0 with 1.0 N aqueous HCl. The mixture was extracted with ethyl acetate (2×20 mL). The combined organic solution was dried (MgSO$_4$), filtered, and concentrated. The residue was purified on a silica gel column eluted with ethyl acetate and hexane to give the desired product (0.384 g).

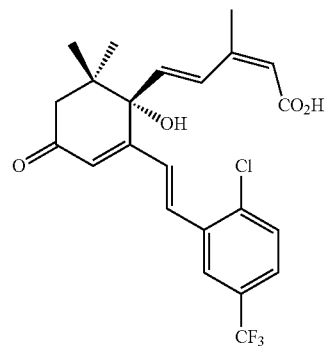

(2Z,4E)-5-((S)-2-((E)-2-chloro-5-(trifluoromethyl)styryl)-1-
hydroxy-6,6-dimethyl-4-oxocyclohex-2-en-1-yl)-3-methylpenta-2,4-
dienoic acid To a solution of Compound 1b (0.38 g, 0.82 mmole) in methanol (15 mL) and water (2 mL) was added lithium hydroxide mono-hydrate (0.4 g, 10 mmole). The mixture was stirred at room temperature overnight and evaporated to remove most of the methanol. Water (10 ml) was added. The resulting mixture was cooled with an ice bath and acidified with 6 N aqueous HCl to pH 2-3, resulting in a white precipitation. The mixture was extracted with ethyl acetate (3×20 ml). The combined organic solution was dried (MgSO$_4$), filtered and evaporated. The residue was purified on a silica gel column eluting with a gradient of ethyl acetate and hexane containing 1% acetic acid. The title compound was obtained as a white solid (0.278 g). $^1$HNMR (CDCl$_3$): δ7.91 (d, 1H), 7.81 (s, 1H), 7.60 (d, 1H), 7.45 (m, 2H), 6.89 (d, 1H), 6.42 (s, 1H), 6.26 (d, 1H), 5.77 (s, 1H), 2.58 (d, 1H), 2.38 (d, 1H), 2.07 (s, 3H), 1.18 (s, 3H), 1.09 (s, 3H). MS (ESI-): m/e=453. Two-dimensional NMR experiments (COSY, NOESY, HSQC and HMBC) confirmed the structure.

Example 2

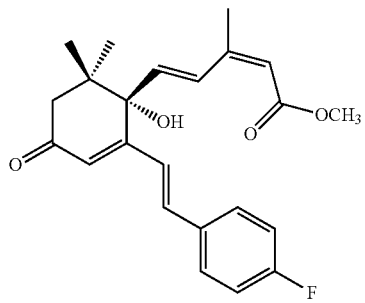

(2Z,4E)-methyl-5-((S)-2-((E)-4-fluorostyryl)-1-
hydroxy-6,6-dimethyl-4-oxocyclohex-2-en-1-yl)-3-
methylpenta-2,4-dienoate The title compound was prepared according to the procedure of Compound 1b, substituting 4-fluorobenzaldehyde for 2-chloro-5-trifluoromethylbenzaldehyde.

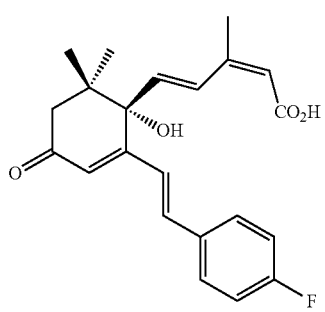

(2Z,4E)-5-((S)-2-((E)-4-fluorostyryl)-1-hydroxy-6,6-
dimethyl-4-oxocyclohex-2-en-1-yl)-3-methylpenta-2,4-dienoic acid The title compound was prepared according to the procedure of Compound 1, substituting Compound 2a for Compound 1b. $^1$HNMR (CDCl$_3$): δ7.92 (d, 1H), 7.43 (m, 2H), 7.18 (d, 1H), 7.03 (m, 2H), 6.77 (d, 1H), 6.34 (s, 1H), 6.26 (d, 1H), 5.77 (s, 1H), 2.56 (d, 1H), 2.36 (d, 1H), 2.11 (s, 3H), 1.15 (s, 3H), 1.07 (s, 3H). MS (ESI-): m/e=369. Two-dimensional NMR experiments (COSY, NOESY, HSQC and HMBC) confirmed the structure.

Example 3

Compound 3a

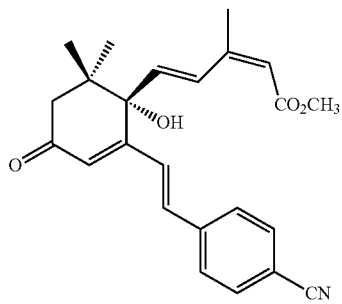

(2Z,4E)-methyl-5-((S)-2-((E)-4-cyanostyryl)-1-hydroxy-6,6-dimethyl-4-oxocyclohex-2-en-1-yl)-3-methylpenta-2,4-dienoate The title compound was prepared according to the procedure of Compound 1b, substituting 4-cyanobenzaldehyde for 2-chloro-5-trifluoromethylbenzaldehyde.

Compound 3

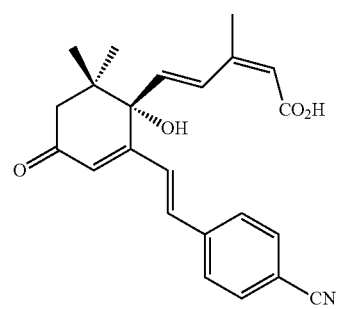

(2Z,4E)-5-((S)-2-((E)-4-cyanostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 3a for Compound 1b. $^1$HNMR (CDCl$_3$): δ7.91 (d, 1H), 7.58 (s, 1H), 7.52 (s, 1H), 7.19 (d, 1H), 6.97 (d, 1H), 6.37 (s, 1H), 6.27 (d, 1H), 5.79 (s, 1H), 2.38 (d, 1H), 2.08 (s, 3H), 1.16 (s, 3H), 1.09 (s, 3H). MS (ESI−): m/e=376. Two-dimensional NMR experiments (COSY, NOESY, HSQC and HMBC) confirmed the structure.

Example 4

Compound 4a

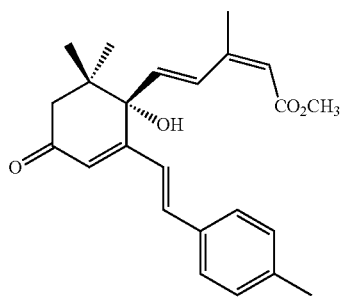

(2Z,4E)-methyl-5-((S)-1-hydroxy-6,6-dimethyl-2-((E)-4-methylstyryl)-4-oxocyclohex-2-en-1-yl)-3-methylpenta-2,4-dienoate The title compound was prepared according to the procedure of Compound 1b, substituting 4-methylbenzaldehyde for 2-chloro-5-trifluoromethylbenzaldehyde.

Compound 4

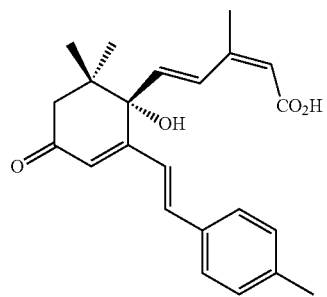

(2Z,4E)-5-((S)-1-hydroxy-6,6-dimethyl-2-((E)-4-methylstyryl)-4-oxocyclohex-2-en-1-yl)-3-methylpenta-2,4-dienoic acid The title compound was prepared according to the procedure of Compound 1, substituting Compound 4a for Compound 1b. $^1$HNMR (CDCl$_3$): δ7.92 (d, 1H), 7.35 (d, 1H), 7.18-7.11 (m, 4H), 6.80 (d, 1H), 6.35 (s, 1H), 6.25 (d, 1H), 5.76 (s, 1H), 2.55 (d, 1H), 2.32 (d, 1H), 2.30 (s, 3H), 2.04 (s, 3H), 1.15 (s, 3H), 1.06 (s, 3H). MS (ESI−): m/e=365. Two-dimensional NMR experiments (COSY, NOESY, HSQC and HMBC) confirmed the structure.

Example 5

Compound 5a

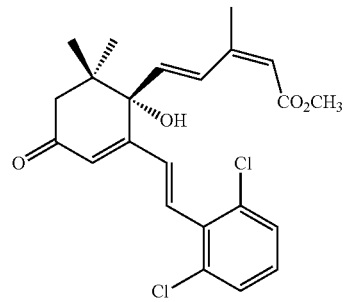

(2Z,4E)-methyl-5-((S)-2-((E)-2,dichlorostyryl)-1-hydroxy-6,6-dimethyl-4-oxocyclohex-2-en-1-yl)-3-methylpenta-2,4-dienoate The title compound was prepared according to the procedure of Compound 1b, substituting 2,6-dichlorobenzaldehyde for 2-chloro-5-trifluoromethylbenzaldehyde.

Compound 5

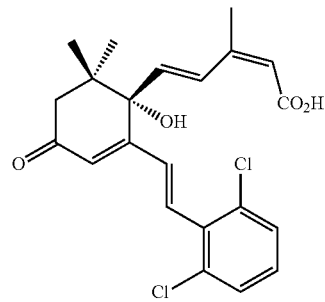

(2Z,4E)-5-((S)-2-((E)-2,6-dichlorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 5a for Compound 1b. ¹HNMR (CDCl₃): δ7.91 (d, 1H), 7.28 (d, 2H), 7.20 (d, 1H), 7.08 (t, 1H), 6.91 (d, 1H), 6.39 (s, 1H), 6.27 (d, 1H), 5.75 (s, 1H), 2.56 (d, 1H), 2.41 (d, 1H), 2.06 (d, 3H), 1.18 (s, 3H), 1.08 (s, 3H). MS (ESI-): m/e=419. Two-dimensional NMR experiments (COSY, NOESY, HSQC and HMBC) confirmed the structure.

Example 6

Compound 6a

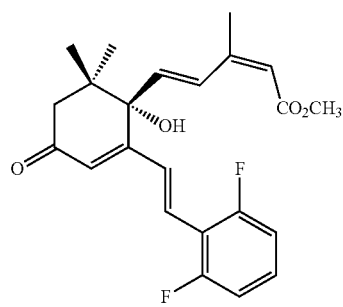

(2Z,4E)-methyl-5-((S)-2-((E)-2,6-difluorostyryl)-1-hydroxy-6,6-dimethyl-4-oxocyclohex-2-en-1-yl)-3-methylpenta-2,4-dienoate The title compound was prepared according to the procedure of Compound 1b, substituting 2, 6-difluorobenzaldehyde for 2-chloro-5-trifluoromethylbenzaldehyde.

Compound 6

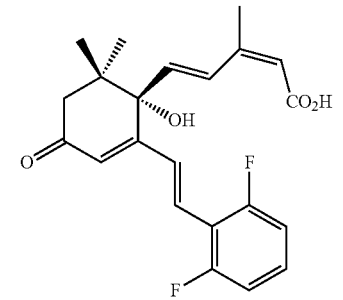

(2Z,4E)-5-((S)-2-((E)-2,6-difluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 6a for Compound 1b. ¹HNMR (CDCl₃): δ7.90 (d, 1H), 7.23 (d, 1H), 7.21-7.15 (m, 2H), 6.85 (t, 2H), 6.39 (s, 1H), 6.27 (d, 1H), 5.75 (s, 1H), 2.56 (d, 1H), 2.39 (d, 1H), 2.06 (d, 3H), 1.16 (s, 3H), 1.07 (s, 3H). MS (ESI-): m/e=387. Two-dimensional NMR experiments (COSY, NOESY, HSQC and HMBC) confirmed the structure.

Example 7

Compound 7a

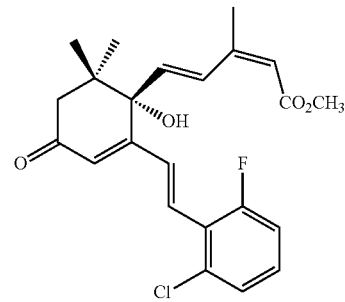

(2Z,4E)-methyl-5-((S)-2-((E)-2-chloro-6-fluorostyryl)-1-hydroxy-6,6-dimethyl-4-oxocyclohex-2-en-1-yl)-3-methylpenta-2,4-dienoate The title compound was prepared according to the procedure of Compound 1b, substituting 2-chloro-6-fluorobenzaldehyde for 2-chloro-5-trifluoromethylbenzaldehyde.

Compound 7

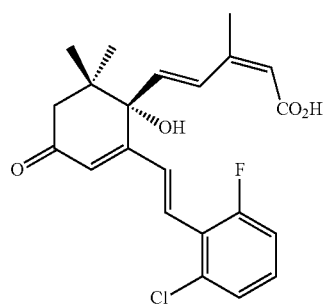

(2Z,4E)-5-((S)-2-((E)-2-chloro-6-fluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 7a for Compound 1b. ¹HNMR (CDCl₃): δ7.92 (d, 1H), 7.37 (d, 1H), 7.20-7.11 (m, 2H), 7.09 (d, 1H), 7.00-6.90 (m, 1H), 6.39 (s, 1H), 6.28 (d, 1H), 5.76 (s, 1H), 2.57 (d, 1H), 2.40 (d, 1H), 2.06 (d, 3H), 1.17 (s, 3H), 1.08 (s, 3H). MS (ESI-): m/e=403. Two-dimensional NMR experiments (COSY, NOESY, HSQC and HMBC) confirmed the structure.

Example 8

Compound 8a

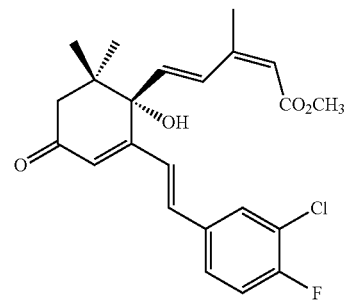

(2Z,4E)-methyl-5-((S)-2-((E)-3-chloro-4-fluorostyryl)-1-hydroxy-6,6-dimethyl-4-oxocyclohex-2-en-1-yl)-3-methylpenta-2,4-dienoate The title compound was prepared according to the procedure of Compound 1b, substituting 3-chloro-4-fluorobenzaldehyde for 2-chloro-5-trifluoromethylbenzaldehyde.

Compound 8

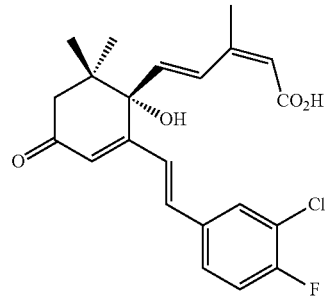

(2Z,4E)-5-((S)-2-((E)-3-chloro-4-fluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 8a for Compound 1b. $^1$HNMR (DMSO-d$_6$): δ12.11 (br s, 1H), 7.77 (d, 1H), 7.73 (dd, 1H), 7.54-7.50 (m, 1H), 7.41 (t, 1H), 7.34 (d, 1H), 6.92 (d, 1H), 6.30 (s, 1H), 6.30 (d, 1H), 5.67 (s, 1H), 5.50 (s, 1H), 2.58 (d, 1H), 2.14 (d, 1H), 1.96 (d, 3H), 0.99 (s, 3H), 0.95 (s, 3H). MS (ESI-): m/e=403. Two-dimensional NMR experiments (COSY, NOESY, HSQC and HMBC) confirmed the structure.

Example 9

Compound 9a

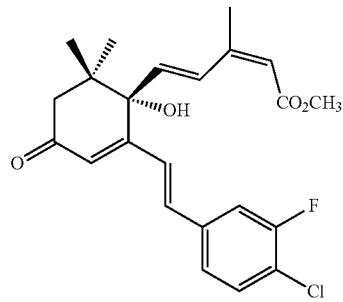

(2Z,4E)-methyl 5-((S)-2-((E)-4-chloro-3-fluorostyryl)-1-hydroxy-6,6-dimethyl-4-oxocyclohex-2-en-1-yl)-3-methylpenta-2,4-dienoate The title compound was prepared according to the procedure of Compound 1b, substituting 4-chloro-3-fluorobenzaldehyde for 2-chloro-5-trifluoromethylbenzaldehyde.

Compound 9

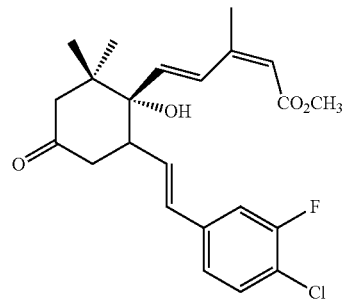

(2Z,4E)-5-((S)-2-((E)-4-chloro-3-fluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 9a for Compound 1b. $^1$HNMR (DMSO-d$_6$): δ12.1 (br s, 1H), 7.79 (d, 1H), 7.59 (t, 1H), 7.56 (dd, 1H), 7.38 (d, 1H), 7.37 (d, 1H), 6.99 (d, 1H), 6.32 (s, 1H), 6.32 (d, 1H), 5.68 (s, 1H), 5.51 (s, 1H), 2.60 (d, 1H), 2.16 (d, 1H), 1.98 (d, 3H), 1.01 (s, 3H), 0.97 (s, 3H). MS (ESI-): m/e=403. Two-dimensional NMR experiments (COSY, NOESY, HSQC and HMBC) confirmed the structure.

Example 10

Compound 10a

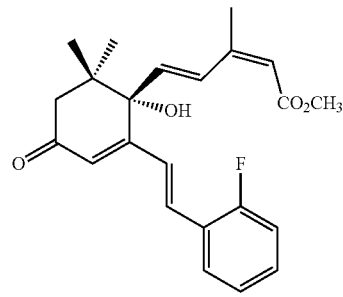

(2Z,4E)-methyl 5-((S)-2-((E)-2-fluorostyryl)-1-hydroxy-6,6-dimethyl-4-oxocyclohex-2-en-1-yl)-3-methylpenta-2,4-dienoate The title compound was prepared according to the procedure of Compound 1b, substituting 2-fluorobenzaldehyde for 2-chloro-5-trifluoromethylbenzaldehyde.

Compound 10

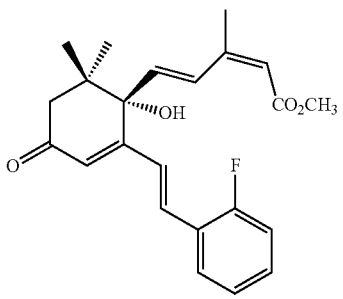

(2Z,4E)-5-((S)-2-((E)-2-fluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 10a for Compound 1b. $^1$HNMR (CDCl$_3$): δ7.91 (d, 1H), 7.52 (dt, 1H), 7.37 (d, 1H), 7.26-7.19 (m, 1H), 7.08 (dt, 1H), 7.01 (ddd, 1H), 6.93 (d, 1H), 6.39 (s, 1H), 6.26 (d, 1H), 5.76 (s, 1H), 2.58 (d, 1H), 2.37 (d, 1H), 2.30 (s, 3H), 2.06 (d, 3H), 1.16 (s, 3H), 1.08 (s, 3H). MS (ESI-): m/e=369. Two-dimensional NMR experiments (COSY, NOESY, HSQC and HMBC) confirmed the structure.

Example 11

Compound 11a

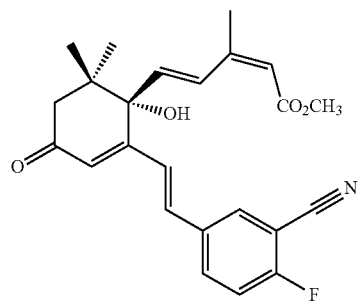

(2Z,4E)-methyl 5-((S)-2-((E)-3-cyano-4-methoxystyryl)-1-hydroxy-6,6-dimethyl-4-oxocyclohex-2-en-1-yl)-3-methylpenta-2,4-dienoate The title compound was prepared according to the procedure of Compound 1b, substituting 2-fluoro-5-formylbenzonitrile for 2-chloro-5-trifluoromethylbenzaldehyde.

Compound 11

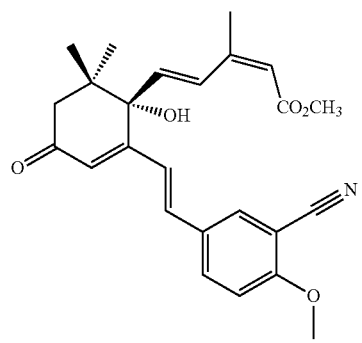

(2Z,4E)-5-((S)-2-((E)-3-cyano-4-methoxystyryl)-1-hydroxy-6,6-dimethyl-4-oxocyclohex-2-en-1-yl)-3-methylpenta-2,4-dienoic acid The title compound was prepared according to the procedure of Compound 1, substituting Compound 11a for Compound 1b. $^1$HNMR (CDCl$_3$): δ7.90 (d, 1H), 7.66 (d, 1H), 7.59 (dd, 1H) 7.13 (d, 1H), 6.91 (d, 1H), 6.79 (d, 1H), 6.36 (s, 1H), 6.25 (d, 1H), 5.77 (s, 1H), 3.92 (s, 3H), 2.58 (d, 1H), 2.35 (d, 1H), 2.07 (d, 3H), 1.16 (s, 3H), 1.09 (s, 3H). MS (ESI-): m/e=406. Two-dimensional NMR experiments (COSY, NOESY, HSQC and HMBC) confirmed the structure.

Example 12

Compound 12a

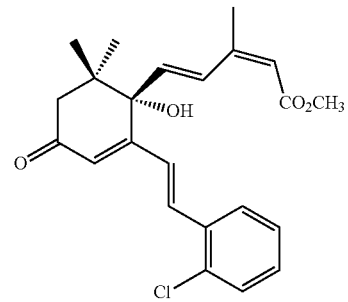

(2Z,4E)-methyl 5-((S)-2-((E)-2-chlorostyryl)-1-hydroxy-6,6-dimethyl-4-oxocyclohex-2-en-1-yl)-3-methylpenta-2,4-dienoate The title compound was prepared according to the procedure of Compound 1b, substituting 2-chlorobenzaldehyde for 2-chloro-5-trifluoromethylbenzaldehyde.

Compound 12

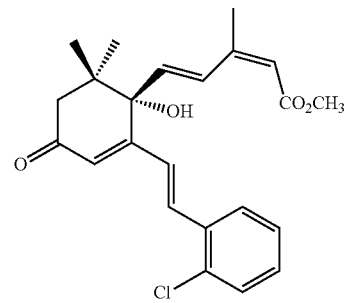

(2Z,4E)-5-((S)-2-((E)-2-chlorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 12a for Compound 1b. $^1$HNMR (CDCl$_3$): δ7.92 (d, 1H), 7.63 (d, 1H), 7.61-7.58 (m, 1H), 7.34-7.31 (m, 1H), 7.22-7.15 (m, 2H), 6.83 (d, 1H), 6.41 (s, 1H), 6.27 (d, 1H), 5.76 (s, 1H), 2.58 (d, 1H), 2.38 (d, 1H), 2.06 (d, 3H), 1.17 (s, 3H), 1.07 (s, 3H). MS (ESI-): m/e=385. Two-dimensional NMR experiments (COSY, NOESY, HSQC and HMBC) confirmed the structure.

Example 13

Compound 13a

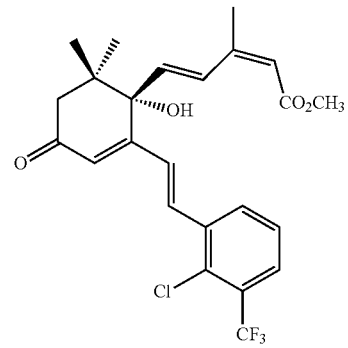

(2Z,4E)-methyl 5-((S)-2-((E)-2-chloro-3-(trifluoromethyl)styryl)-1-hydroxy-6,6-dimethyl-4-oxocyclohex-2-en-1-yl)-3-methylpenta-2,4-dienoate The title compound was prepared according to the procedure of Compound 1b, substituting 2-chloro-3-(trifluoromethyl)benzaldehyde for 2-chloro-5-trifluoromethylbenzaldehyde.

Compound 13

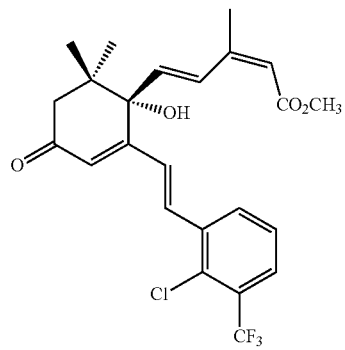

(2Z,4E)-5-((S)-2-((E)-2-chloro-3-(trifluromethyl)styryl)-1-hydroxy-6,6-dimethyl-4-oxocyclohex-2-en-1-yl)-3-methylpenta-2,4-dienic acid The title compound was prepared according to the procedure of Compound 1, substituting Compound 13a for Compound 1b. ¹HNMR (CDCl₃): δ7.91 (d, 1H), 7.76 (dd, 1H), 7.68 (d, 1H), 7.60 (dd, 1H), 7.31 (t, 1H), 6.84 (d, 1H), 6.41 (s, 1H), 6.27 (d, 1H), 5.77 (s, 1H), 2.59 (d, 1H), 2.38 (d, 1H), 2.07 (d, 3H), 1.18 (s, 3H), 1.09 (s, 3H). MS (ESI−): m/e=453. Two-dimensional NMR experiments (COSY, NOESY, HSQC and HMBC) confirmed the structure.

Example 14

Compound 14a

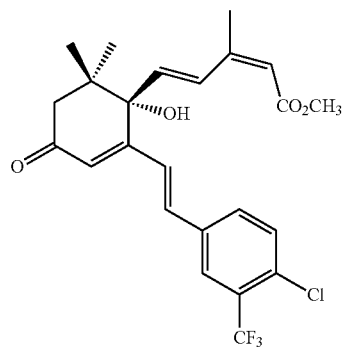

(2Z,4E)-methyl 5-((S)-2-((E)-4-chloro-3-(trifluoromethyl)styryl)-1-hydroxy-6,6-dimethyl-4-oxocyclohex-2-en-1-yl)-3-methylpenta-2,4-dienoate The title compound was prepared according to the procedure of Compound 1b, substituting 4-chloro-3-(trifluoromethyl)benzaldehyde for 2-chloro-5-trifluoromethylbenzaldehyde.

Compound 14

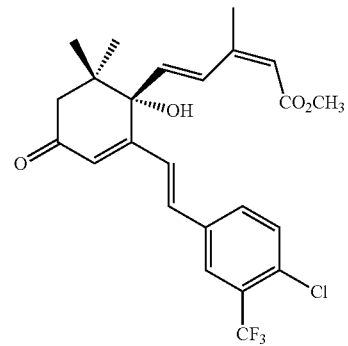

(2Z,4E)-5-((S)-2-((E)-4-chloro-3-(trifluoromethyl)styryl)-1-hydroxy-6,6-dimethyl-4-oxocyclohex-2-en-1-yl)-3-methylpenta-2,4-dienoic acid The title compound was prepared according to the procedure of Compound 1, substituting Compound 14a for Compound 1b. ¹HNMR (CDCl₃): δ7.89 (d, 1H), 7.71 (d, 1H), 7.53 (dd, 1H), 7.42 (d, 1H), 7.19 (d, 1H), 6.90 (d, 1H), 6.37 (s, 1H), 6.25 (d, 1H), 5.77 (s, 1H), 2.57 (d, 1H), 2.36 (d, 1H), 2.07 (d, 3H), 1.16 (s, 3H), 1.09 (s, 3H). MS (ESI−): m/e=453. Two-dimensional NMR experiments (COSY, NOESY, HSQC and HMBC) confirmed the structure.

Example 15

Compound 15a

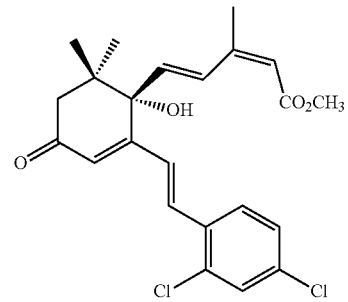

(2Z,4E)-methyl 5-((S)-2-((E)-2,4-dichlorostyryl)-1-hydroxy-6,6-dimethyl-4-oxocyclohex-2-en-1-yl)-3-methylpenta-2,4-dienoate The title compound was prepared according to the procedure of Compound 1b, substituting 2,4-dichlorobenzaldehyde for 2-chloro-5-trifluoromethylbenzaldehyde.

Compound 15

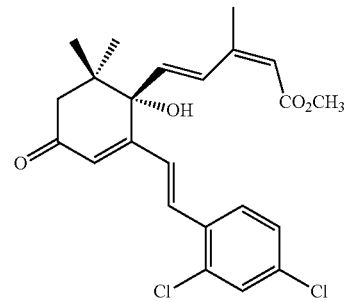

(2Z,4E)-5-((S)-2-((E)-2,4-dichlorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 15a for Compound 1b. ¹HNMR (CDCl₃): δ7.91 (d, 1H), 7.54 (d, 1H), 7.52 (d, 1H), 7.33 (d, 1H), 7.17 (dd, 1H), 6.82 (d, 1H), 6.39 (s, 1H), 6.27 (d, 1H), 5.77 (s, 1H), 2.58 (d, 1H), 2.37 (d, 1H), 2.07 (d, 3H), 1.17 (s, 3H), 1.08 (s, 3H). MS (ESI−): m/e=419. Two-dimensional NMR experiments (COSY, NOESY, HSQC and HMBC) confirmed the structure.

Example 16

Compound 16a

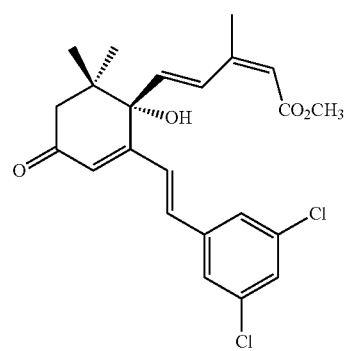

(2Z,4E)-methyl 5-((S)-2-((E)-3,5-dichlorostyryl)-1-hydroxy-6,6-dimethyl-4-oxocyclohex-2-en-1-yl)-3-methylpenta-2,4-dienoate The title compound was prepared according to the procedure of Compound 1b, substituting 3,5-dichlorobenzaldehyde for 2-chloro-5-trifluoromethylbenzaldehyde.

Compound 16

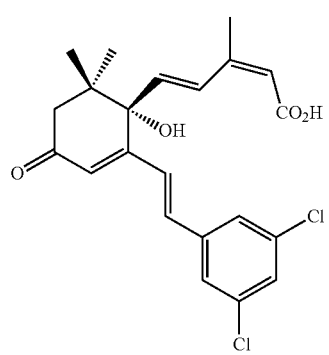

(2Z,4E)-5-((S)-2-((E)-3,5-dichlorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 16a for Compound 1b. ¹HNMR (CDCl₃): δ7.88 (d, 1H), 7.29 (d, 1H), 7.22 (t, 1H), 7.07 (d, 1H), 6.86 (d, 1H), 6.35 (s, 1H), 6.23 (d, 1H), 5.77 (s, 1H), 2.57 (d, 1H), 2.35 (d, 1H), 2.06 (d, 3H), 1.16 (s, 3H), 1.08 (s, 3H). MS (ESI−): m/e=419. Two-dimensional NMR experiments (COSY, NOESY, HSQC and HMBC) confirmed the structure.

Example 17

Compound 17a

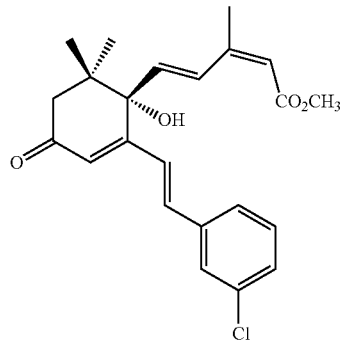

(2Z,4E)-methyl 5-((S)-2-((E)-3,5-chlorostyryl)-1-hydroxy-6,6-dimethyl-4-oxocyclohex-2-en-1-yl)-3-methylpenta-2,4-dienoate The title compound was prepared according to the procedure of Compound 1b, substituting 3-chlorobenzaldehyde for 2-chloro-5-trifluoromethylbenzaldehyde.

Compound 17

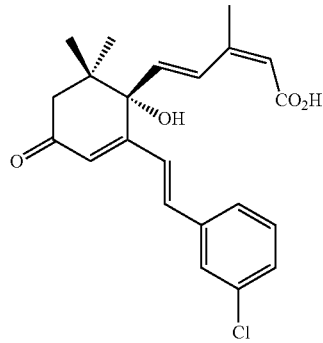

(2Z,4E)-5-((S)-2-((E)-3-chlorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 17a for Compound 1b. ¹HNMR (DMSO-d₆): δ7.80 (d, 1H), 7.59 (t, 1H), 7.49 (dt, 1H), 7.40 (d, 1H), 7.38-7.34 (m, 2H), 6.99 (d, 1H), 6.34 (s, 1H), 6.32 (d, 1H), 5.68 (s, 1H), 5.52 (s, 1H), 2.59 (d, 1H), 2.17 (d, 1H), 1.98 (d, 3H), 1.01 (s, 3H), 0.97 (s, 3H). MS (ESI−): m/e=385. Two-dimensional NMR experiments (COSY, NOESY, HSQC and HMBC) confirmed the structure.

Example 18

Compound 18a

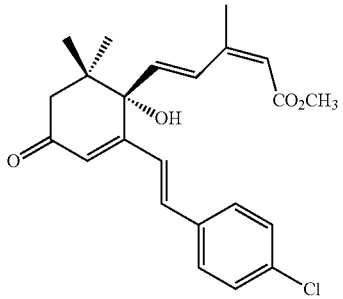

(2Z,4E)-methyl 5-((S)-2-((E)-4-chlorostyryl)-1-hydroxy-6,6-dimethyl-4-oxocyclohex-2-en-1-yl)-3-methylpenta-2,4-dienoate The title compound was prepared according to the procedure of Compound 1b, substituting 4-chlorobenzaldehyde for 2-chloro-5-trifluoromethylbenzaldehyde.

Compound 18

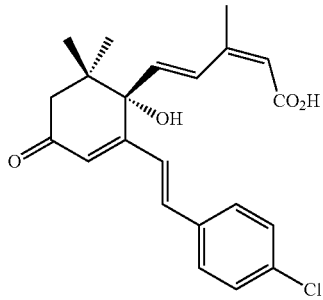

(2Z,4E)-5-((S)-2-((E)-4-chlorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 18a for Compound 1b. $^1$HNMR (CDCl$_3$): δ7.89 (d, 1H), 7.35 (d, 2H), 7.25 (d, 2H), 7.14 (d, 1H), 6.82 (d, 1H), 6.35 (s, 1H), 6.22 (d, 1H), 5.75 (s, 1H), 2.56 (d, 1H), 2.36 (d, 1H), 2.03 (d, 3H), 1.14 (s, 3H), 1.06 (s, 3H). MS (ESI-): m/e=385. Two-dimensional NMR experiments (COSY, NOESY, HSQC and HMBC) confirmed the structure.

Example 19

Compound 19a

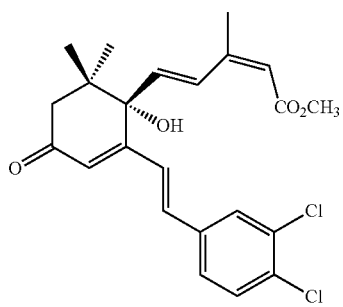

(2Z,4E)-methyl 5-((S)-2-((E)-3-4-dichlorostyryl)-1-hydroxy-6,6-dimethyl-4-oxocyclohex-2-en-1-yl)-3-methylpenta-2,4-dienoate The title compound was prepared according to the procedure of Compound 1b, substituting 3,4-dichlorobenzaldehyde for 2-chloro-5-trifluoromethylbenzaldehyde.

Compound 19

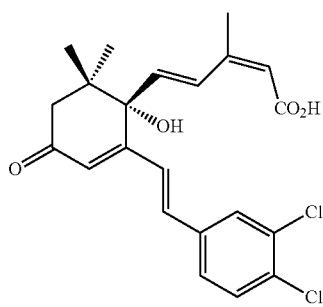

(2Z,4E)-5-((S)-2-((E)-3,4-dichlorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 19a for Compound 1b. $^1$HNMR (DMSO-d$_6$): δ7.79 (d, 1H), 7.78 (d, 1H), 7.64 (d, 1H), 7.52 (dd, 1H), 7.37 (d, 1H), 7.01 (d, 1H), 6.34 (s, 1H), 6.32 (d, 1H), 5.69 (s, 1H), 5.53 (s, 1H), 2.60 (d, 1H), 2.17 (d, 1H), 1.98 (d, 3H), 1.01 (s, 3H), 0.97 (s, 3H). MS (ESI-): m/e=419. Two-dimensional NMR experiments (COSY, NOESY, HSQC and HMBC) confirmed the structure.

Example 20

Compound 20a

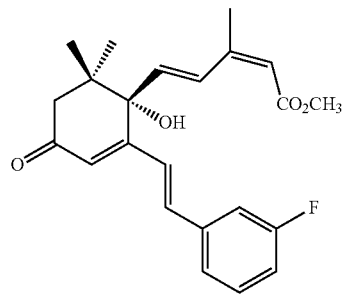

(2Z,4E)-methyl 5-((S)-2-((E)-3-fluorostyryl)-1-hydroxy-6,6-dimethyl-4-oxocyclohex-2-en-1-yl)-3-methylpenta-2,4-dienoate The title compound was prepared according to the procedure of Compound 1b, substituting 3-fluorobenzaldehyde for 2-chloro-5-trifluoromethylbenzaldehyde.

Compound 20

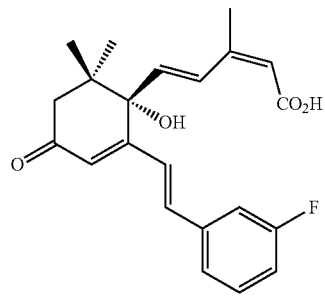

(2Z,4E)-5-((S)-2-((E)-3-fluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 20a for Compound 1b. $^1$HNMR (DMSO-d$_6$): δ12.10 (br s, 1H), 7.81 (d, 1H), 7.46-7.32 (m, 4H), 7.14 (t, 1H), 6.97 (d, 1H), 6.33 (s, 1H), 6.32 (d, 1H), 5.68 (s, 1H), 5.51 (s, 1H), 2.60 (d, 1H), 2.17 (d, 1H), 1.98 (s, 3H), 1.01 (s, 3H), 0.97 (s, 3H). MS (ESI-): m/e=369. Two-dimensional NMR experiments (COSY, NOESY, HSQC and HMBC) confirmed the structure.

Example 21

Compound 21a

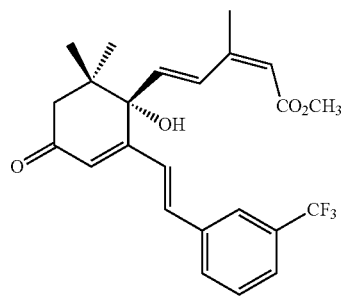

(2Z,4E)-methyl 5-((S)-1-hydroxy-6,6-dimethyl-4-oxo-2-((E)-3-(trifluoromethyl)styryl)cyclohex-2-en-1-yl)-3-methylpenta-2,4-dienoate The title compound was prepared according to the procedure of Compound 1b, substituting 3-(trifluoromethyl)benzaldehyde for 2-chloro-5-trifluoromethylbenzaldehyde.

Compound 21

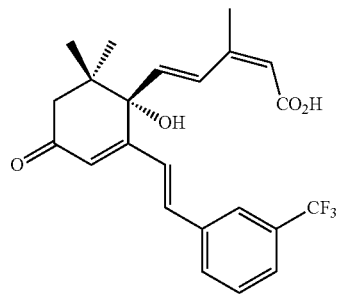

(2Z,4E)-5-((S)-1-hydroxy-6,6-dimethyl-4-oxo-2-((E)-3-(trifluoromethyl)styryl)cyclohex-2-en-1-yl)-3-methylpenta-2,4-dienoic acid The title compound was prepared according to the procedure of Compound 1, substituting Compound 21a for Compound 1b. $^1$HNMR (CDCl$_3$): δ7.90 (d, 1H), 7.66 (s, 1H), 7.61 (d, 1H), 7.49 (d, 1H), 7.41 (t, 1H), 7.23 (d, 1H), 6.92 (d, 1H), 6.39 (s, 1H), 6.25 (d, 1H), 5.76 (s, 1H), 2.58 (d, 1H), 2.36 (d, 1H), 2.06 (d, 3H), 1.16 (s, 3H), 1.08 (s, 3H). MS (ESI-): m/e=419. Two-dimensional NMR experiments (COSY, NOESY, HSQC and HMBC) confirmed the structure.

Example 22

Compound 22a

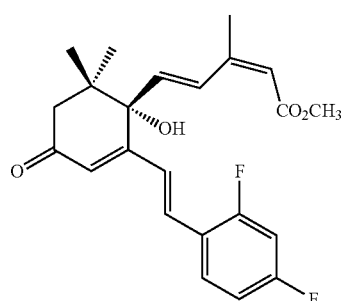

(2Z,4E)-methyl 5-((S)-2-((E)-2,4-difluorostyryl)-1-hydroxy-6,6-dimethyl-4-oxocyclohex-2-en-1-yl)-3-methylpenta-2,4-dienoate The title compound was prepared according to the procedure of Compound 1b, substituting 2,4-difluorobenzaldehyde for 2-chloro-5-trifluoromethylbenzaldehyde.

Compound 22

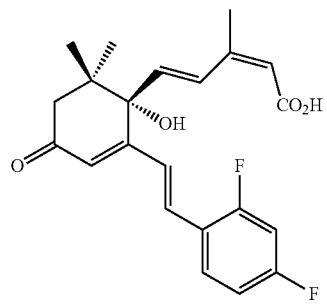

(2Z,4E)-5-((S)-2-((E)-2,4-difluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 22a for Compound 1b. $^1$HNMR (DMSO-d$_6$): δ12.06 (br s, 1H), 7.80 (d, 1H), 7.71 (dt, 1H), 7.35 (d, 1H), 7.32-7.25 (m, 1H), 7.13 (dt, 1H), 6.97 (d, 1H), 6.32 (d, 1H), 6.31 (s, 1H), 5.68 (s, 1H), 5.51 (s, 1H), 2.58 (d, 1H), 2.19 (d, 1H), 1.98 (d, 3H), 1.01 (s, 3H), 0.96 (s, 3H). MS (ESI-): m/e=387. Two-dimensional NMR experiments (COSY, NOESY, HSQC and HMBC) confirmed the structure.

Example 23

Compound 23a

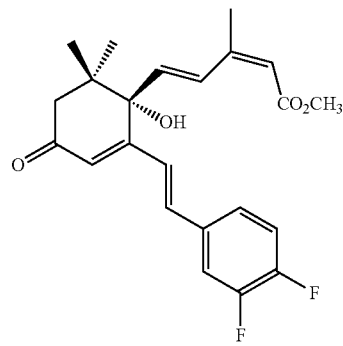

(2Z,4E)-methyl 5-((S)-2-((E)-3,4-difluorostyryl)-1-hydroxy-6,6-dimethyl-4-oxocyclohex-2-en-1-yl)-3-methylpenta-2,4-dienoate The title compound was prepared according to the procedure of Compound 1b, substituting 3,4-difluorobenzaldehyde for 2-chloro-5-trifluoromethylbenzaldehyde.

Compound 23

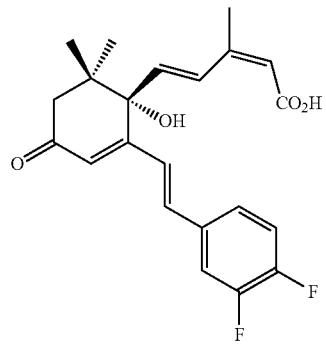

(2Z,4E)-5-((S)-2-((E)-3,4-difluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 23a for Compound 1b. $^1$HNMR (DMSO-$d_6$): δ12.10 (br s, 1H), 7.79 (d, 1H), 7.58 (ddd, 1H), 7.47-7.34 (m, 2H), 7.35 (d, 1H), 6.92 (d, 1H), 6.31 (d, 1H), 6.30 (s, 1H), 5.68 (s, 1H), 5.50 (s, 1H), 2.59 (d, 1H), 2.16 (d, 1H), 1.98 (d, 3H), 1.01 (s, 3H), 0.97 (s, 3H). MS (ESI−): m/e=387. Two-dimensional NMR experiments (COSY, NOESY, HSQC and HMBC) confirmed the structure.

Example 24

Compound 24a

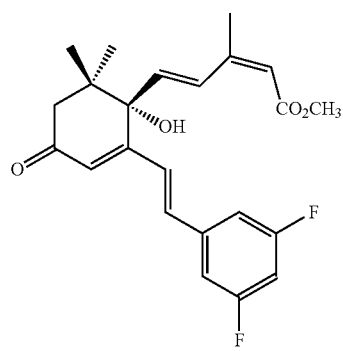

(2Z,4E)-methyl 5-((S)-2-((E)-3,5-difluorostyryl)-1-hydroxy-6,6-dimethyl-4-oxocyclohex-2-en-1-yl)-3-methylpenta-2,4-dienoate The title compound was prepared according to the procedure of Compound 1b, substituting 3,5-difluorobenzaldehyde for 2-chloro-5-trifluoromethylbenzaldehyde.

Compound 24

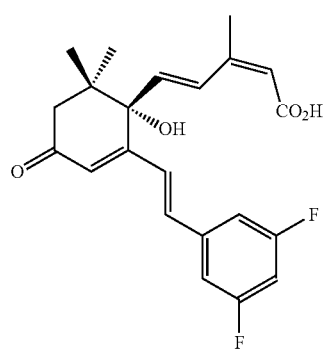

(2Z,4E)-5-((S)-2-((E)-3,5-difluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 24a for Compound 1b. $^1$HNMR (DMSO-$d_6$): δ12.13 (br s, 1H), 7.80 (d, 1H), 7.37 (d, 1H), 7.24 (dd, 2H), 7.16 (tt, 1H), 7.02 (d, 1H), 6.32 (d, 1H), 6.32 (s, 1H), 5.69 (s, 1H), 5.52 (s, 1H), 2.61 (d, 1H), 2.17 (d, 1H), 1.99 (d, 3H), 1.01 (s, 3H), 0.97 (s, 3H). MS (ESI−): m/e=387. Two-dimensional NMR experiments (COSY, NOESY, HSQC and HMBC) confirmed the structure.

Example 25

Compound 25a

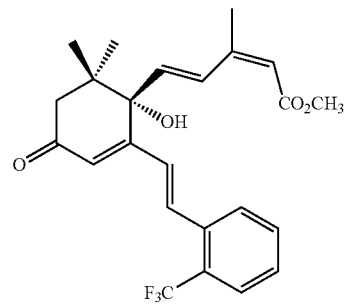

(2Z,4E)-methyl 5-((S)-1-hydroxy-6,6-dimethyl-4-oxo-2-((E)-2-(trifluoromethyl)styryl)cyclohex-2-en-1-yl)-3-methylpenta-2,4-dienoate The title compound was prepared according to the procedure of Compound 1b, substituting 2-(trifluoromethyl)benzaldehyde for 2-chloro-5-trifluoromethylbenzaldehyde.

Compound 25

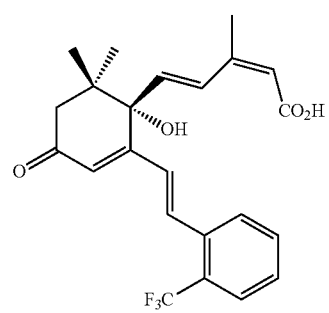

(2Z,4E)-5-((S)-2-((E)-3,5-difluorostyryl)-1-hydroxy-6,6-dimethyl-4-oxocyclohex-2-en-1-yl)-3-methylpenta-2,4-dienoic acid The title compound was prepared according to the procedure of Compound 1, substituting Compound 25a for Compound 1b. $^1$HNMR (CDCl$_3$): δ7.90 (d, 1H), 7.68 (d, 1H), 7.61-7.53 (m, 2H), 7.47 (t, 1H), 7.33 (t, 1H), 6.80 (d, 1H), 6.35 (s, 1H), 6.27 (d, 1H), 5.76 (s, 1H), 2.58 (d, 1H), 2.37 (d, 1H), 2.06 (d, 3H), 1.17 (s, 3H), 1.08 (s, 3H). MS (ESI−): m/e=419. Two-dimensional NMR experiments (COSY, NOESY, HSQC and HMBC) confirmed the structure.

Example 26

Compound 26a

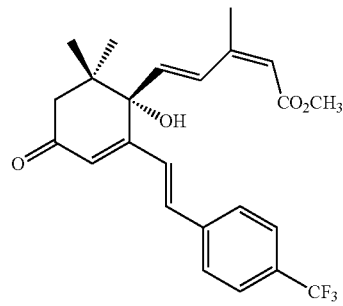

(2Z,4E)-methyl 5-((S)-1-hydroxy-6,6-dimethyl-4-oxo-2-((E)-4-(trifluoromethyl)styryl)cyclohex-2-en-1-yl)-3-methylpenta-2,4-dienoate The title compound was prepared according to the procedure of Compound 1b, substituting 4-(trifluoromethyl)benzaldehyde for 2-chloro-5-trifluoromethylbenzaldehyde.

Compound 26

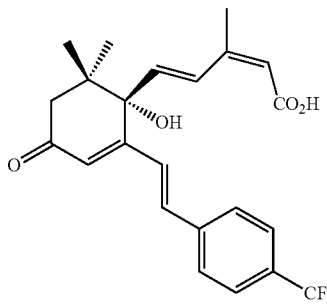

(2Z,4E)-5-((S)-1-hydroxy-6,6-dimethyl-4-oxo-2-((E)-4-(trifluoromethyl)styryl)cyclohex-2-en-1-yl)-3-methylpenta-2,4-dienoic acid The title compound was prepared according to the procedure of Compound 1, substituting Compound 26a for Compound 1b. $^1$HNMR (CDCl$_3$): δ7.93 (d, 1H), 7.52 (m, 4H), 7.22 (d, 1H), 6.96 (d, 1H), 6.39 (s, 1H), 6.27 (d, 1H), 5.77 (s, 1H), 2.59 (d, 1H), 2.37 (d, 1H), 2.07 (d, 3H), 1.16 (s, 3H), 1.08 (s, 3H). MS (ESI-): m/e=419. Two-dimensional NMR experiments (COSY, NOESY, HSQC and HMBC) confirmed the structure.

Example 27

Compound 27a

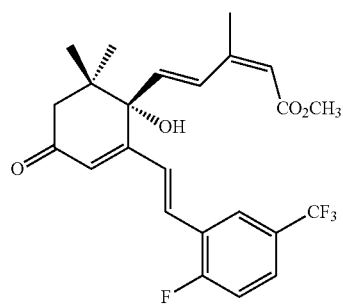

(2Z,4E)-methyl 5-((S)-2-((E)-2-fluoro-5-(trifluoromethyl)styryl)-1-hydroxy-6,6-dimethyl-4-oxocyclohex-2-en-1-yl)-3-methylpenta-2,4-dienoate The title compound was prepared according to the procedure of Compound 1b, substituting 2-fluoro-5-(trifluoromethyl)benzaldehyde for 2-chloro-5-trifluoromethylbenzaldehyde.

Compound 27

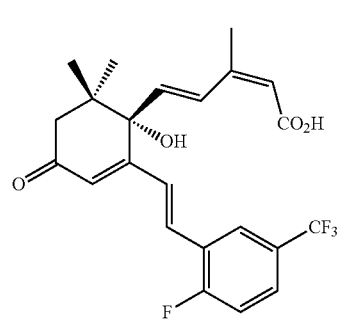

(2Z,4E)-5-((S)-2-((E)-2-fluoro-5-(trifluoromethyl)styryl)-1-hydroxy-6,6-dimethyl-4-oxocyclohex-2-en-1-yl)-3-methylpenta-2,4-dienoic acid The title compound was prepared according to the procedure of Compound 1, substituting Compound 27a for Compound 1b. $^1$HNMR (CDCl$_3$): δ7.90 (d, 1H), 7.78 (dd, 1H), 7.51-7.46 (m, 1H), 7.34 (d, 1H), 7.12 (t, 1H), 6.99 (d, 1H), 6.40 (s, 1H), 6.25 (d, 1H), 5.77 (s, 1H), 2.58 (d, 1H), 2.37 (d, 1H), 2.07 (d, 3H), 1.17 (s, 3H), 1.09 (s, 3H). MS (ESI-): m/e=327 (fragment+HCOO-). Two-dimensional NMR experiments (COSY, NOESY, HSQC and HMBC) confirmed the structure.

Example 28

Compound 28

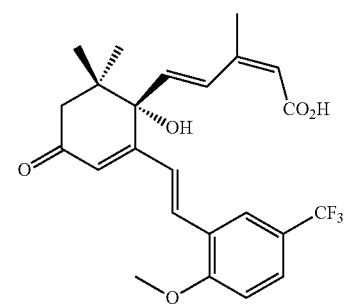

(2Z,4E)-5-((S)-1-hydroxy-2-((E)-2-methoxy-5-(trifluoromethyl)styryl)-6,6-dimethyl-4-oxocyclohex-2-en-1-yl)-3-methylpenta-2,4-dienoic acid The title compound was isolated as one of the products from the preparation of Compound 27 from Compound 27a. $^1$HNMR (CDCl$_3$): δ7.92 (d, 1H), 7.72 (d, 1H), 7.53 (d, 1H), 7.48 (dd, 1H), 6.93 (d, 1H), 6.89 (d, 1H), 6.41 (s, 1H), 6.26 (d, 1H), 5.76 (s, 1H), 3.87 (s, 3H), 2.57 (d, 1H), 2.38 (d, 1H), 2.06 (d, 3H), 1.16 (s, 3H), 1.08 (s, 3H). MS (ESI-): m/e=449. Two-dimensional NMR experiments (COSY, NOESY, HSQC and HMBC confirmed the structure.

Example 29

Compound 29a

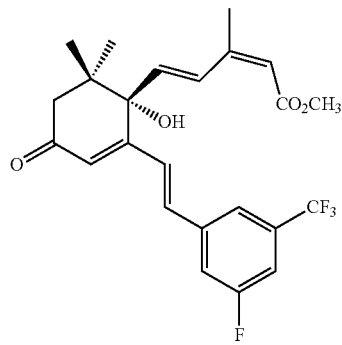

(2Z,4E)-methyl 5-((S)-2-((E)-3-fluoro-5-(trifluoromethyl)styryl)-1-hydroxy-6,6-dimethyl-4-oxocyclohex-2-en-1-yl)-3-methylpenta-2,4-dienoate The title compound was prepared according to the procedure of Compound 1b, substituting 3-fluoro-5-(trifluoromethyl)benzaldehyde for 2-chloro-5-trifluoromethylbenzaldehyde.

Compound 29

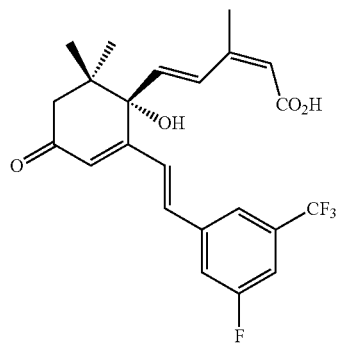

(2Z,4E)-5-((S)-2-((E)-3-fluoro-5-(trifluoromethyl)styryl)-1-hydroxy-6,6-dimethyl-4-oxocyclohex-2-en-1-yl)-3-methylpenta-2,4-dienoic acid The title compound was prepared according to the procedure of Compound 1, substituting Compound 29a for Compound 1b. $^1$HNMR (CDCl$_3$): δ7.88 (d, 1H), 7.46 (s, 1H), 7.33 (dt, 1H), 7.20 (dt, 1H), 7.19 (d, 1H), 6.92 (d, 1H), 6.38 (s, 1H), 6.24 (d, 1H), 5.77 (s, 1H), 2.57 (d, 1H), 2.36 (d, 1H), 2.06 (d, 3H), 1.16 (s, 3H), 1.08 (s, 3H). MS (ESI−): m/e=437. Two-dimensional NMR experiments (COSY, NOESY, HSQC and HMBC) confirmed the structure.

Example 30

Compound 30a

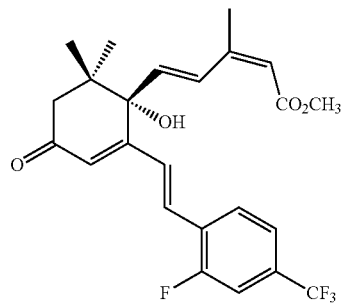

(2Z,4E)-methyl 5-((S)-2-((E)-2-fluoro-4-(trifluoromethyl)styryl)-1-hydroxy-6,6-dimethyl-4-oxocyclohex-2-en-1-yl)-3-methylpenta-2,4-dienoate The title compound was prepared according to the procedure of Compound 1b, substituting 2-fluoro-4-(trifluoromethyl)benzaldehyde for 2-chloro-5-trifluoromethylbenzaldehyde.

Compound 30

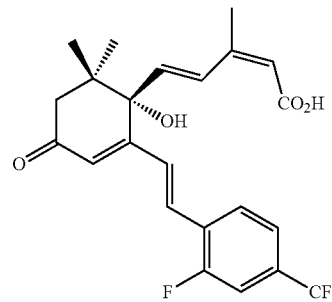

(2Z,4E)-5-((S)-2-((E)-2-fluoro-4-(trifluoromethyl)styryl)-1-hydroxy-6,6-dimethyl-4-oxocyclohex-2-en-1-yl)-3-methylpenta-2,4-dienoic acid The title compound was prepared according to the procedure of Compound 1, substituting Compound 30a for Compound 1b. $^1$HNMR (CDCl$_3$): δ7.92 (d, 1H), 7.63 (t, 1H), 7.34 (d, 1H), 7.34 (d, 1H), 7.26 (d, 1H), 7.03 (d, 1H), 6.40 (s, 1H), 6.27 (d, 1H), 5.77 (s, 1H), 2.59 (d, 1H), 2.38 (d, 1H), 2.07 (d, 3H), 1.17 (s, 3H), 1.09 (s, 3H). MS (ESI−): m/e=437. Two-dimensional NMR experiments (COSY, NOESY, HSQC and HMBC) confirmed the structure.

Example 31

Compound 31a

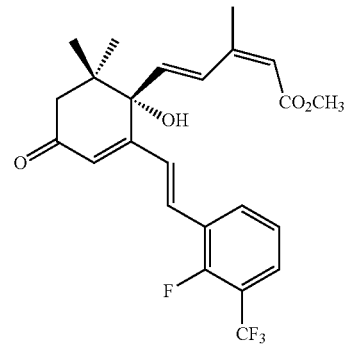

(2Z,4E)-methyl 5-((S)-2-((E)-2-fluoro-3-(trifluoromethyl)styryl)-1-hydroxy-6,6-dimethyl-4-oxocyclohex-2-en-1-yl)-3-methylpenta-2,4-dienoate The title compound was prepared according to the procedure of Compound 1b, substituting 2-fluoro-3-(trifluoromethyl)benzaldehyde for 2-chloro-5-trifluoromethylbenzaldehyde.

31

Compound 31

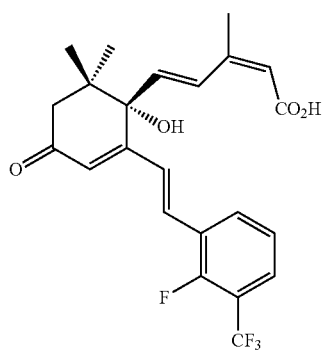

(2Z,4E)-5-((S)-2-((E)-2-fluoro-3-(trifluoromethyl)styryl)-1-hydroxy-6,6-dimethyl-4-oxocyclohex-2-en-1-yl)-3-methylpenta-2,4-dienoic acid The title compound was prepared according to the procedure of Compound 1, substituting Compound 31a for Compound 1b. $^1$HNMR (CDCl$_3$): δ7.90 (d, 1H), 7.72 (t, 1H), 7.49 (t, 1H), 7.36 (d, 1H), 7.18 (d, 1H), 6.98 (d, 1H), 6.40 (s, 1H), 6.26 (d, 1H), 5.77 (s, 1H), 2.59 (d, 1H), 2.38 (d, 1H), 2.07 (d, 3H), 1.17 (s, 3H), 1.09 (s, 3H). MS (ESI−): m/e=437. Two-dimensional NMR experiments (COSY, NOESY, HSQC and HMBC) confirmed the structure.

Example 32

Compound 32a

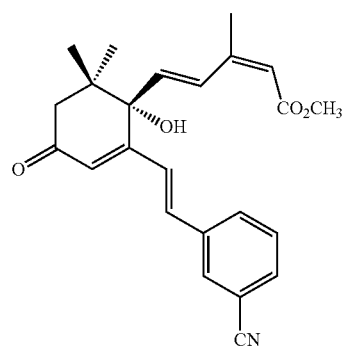

(2Z,4E)-methyl 5-((S)-2-((E)-3-cyanostyryl)-1-hydroxy-6,6-dimethyl-4-oxocyclohex-2-en-1-yl)-3-methylpenta-2,4-dienoate The title compound was prepared according to the procedure of Compound 1b, substituting 3-formylbenzonitrile for 2-chloro-5-trifluoromethylbenzaldehyde.

Compound 32

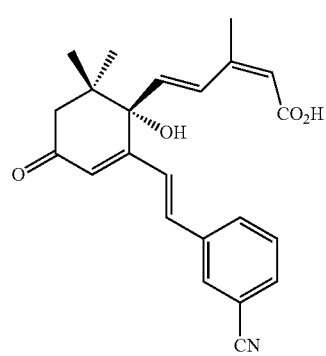

(2Z,4E)-5-((S)-2-((E)-3-cyanostyryl)-1-hydroxy-6,6-dimethyl-4-oxocyclohex-2-en-1-yl)-3-methylpenta-2,4-dienoic acid

32

The title compound was prepared according to the procedure of Compound 1, substituting Compound 32a for Compound 1b. $^1$HNMR (CDCl$_3$): δ7.91 (d, 1H), 7.74 (s, 1H), 7.65 (dt, 1H), 7.51 (dt, 1H), 7.41 (t, 1H), 7.19 (d, 1H), 6.94 (dd, 1H), 6.38 (s, 1H), 6.25 (d, 1H), 5.78 (s, 1H), 2.58 (d, 1H), 2.37 (d, 1H), 2.06 (d, 3H), 1.17 (s, 3H), 1.09 (s, 3H). MS (ESI−): m/e=376. Two-dimensional NMR experiments (COSY, NOESY, HSQC and HMBC) confirmed the structure.

Example 33

Compound 33a

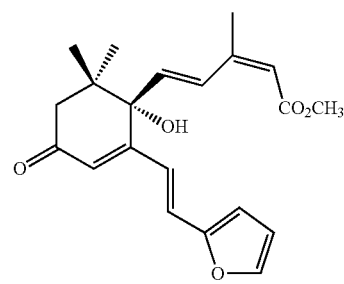

(2Z,4E)-methyl 5-((S)-2-((E)-2-(furan-2-yl)vinyl)-1-hydroxy-6,6-dimethyl-4-oxocyclohex-2-en-1-yl)-3-methylpenta-2,4-dienoate The title compound was prepared according to the procedure of Compound 1b, substituting furfural for 2-chloro-5-trifluoromethylbenzaldehyde.

Compound 33

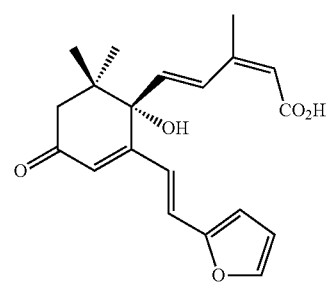

(2Z,4E)-5-((S)-2-((E)-2-(furan-2-yl)vinyl)-1-hydroxy-6,6-dimethyl-4-oxocyclohex-2-en-1-yl)-3-methylpenta-2,4-dienoic acid The title compound was prepared according to the procedure of Compound 1, substituting Compound 33a for Compound 1b. $^1$HNMR (CDCl$_3$): δ7.91 (d, 1H), 7.43 (s, 1H), 7.10 (d, 1H), 6.75 (d, 1H), 6.47 (d, 1H), 6.42 (t, 1H), 6.32 (s, 1H), 6.26 (d, 1H), 5.77 (s, 1H), 2.56 (d, 1H), 2.36 (d, 1H), 2.07 (s, 3H), 1.17 (s, 3H), 1.08 (s, 3H). MS (ESI−): m/e=341. Two-dimensional NMR experiments (COSY, NOESY, HSQC and HMBC) confirmed the structure.

Example 34

Compound 34a

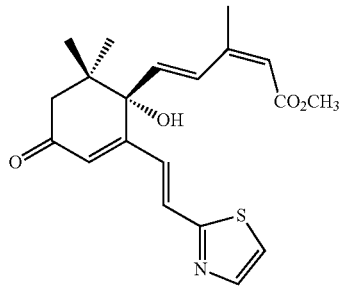

(2Z,4E)-methyl 5-((S)-1-hydroxy-6,6-dimethyl-4-oxo-2-((E)-2-(thiazol-2-yl)vinyl)cyclohex-2-en-1-yl)-3-methylpenta-2,4-dienoate The title compound was prepared according to the procedure of Compound 1b, substituting 2-thiazolecarboxaldehyde for 2-chloro-5-trifluoromethylbenzaldehyde.

Compound 34

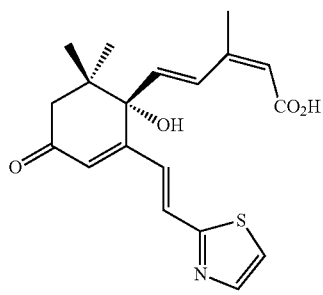

(2Z,4E)-5-((S)-1-hydroxy-6,6-dimethyl-4-oxo-2-((E)-2-(thiazol-2-yl)vinyl)cyclohex-2-en-1-yl)-3-methylpenta-2,4-dienoic acid The title compound was prepared according to the procedure of Compound 1, substituting Compound 34a for Compound 1b. $^1$HNMR (DMSO-$d_6$): δ12.05 (br s, 1H), 7.90 (d, 1H), 7.81 (d, 1H), 7.77 (d, 1H), 7.57 (d, 1H), 7.11 (d, 1H), 6.43 (s, 1H), 6.32 (d, 1H), 5.69 (s, 1H), 5.59 (s, 1H), 2.60 (d, 1H), 2.20 (d, 1H), 1.98 (d, 3H), 1.01 (s, 3H), 0.97 (s, 3H). MS (ESI−): m/e=358. Two-dimensional NMR experiments (COSY, NOESY, HSQC and HMBC) confirmed the structure.

Example 35

Compound 35a

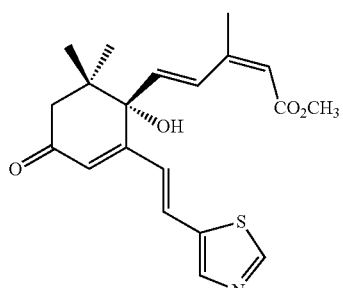

(2Z,4E)-methyl 5-((S)-1-hydroxy-6,6-dimethyl-4-oxo-2-((E)-2-(thiazol-5-yl)vinyl)cyclohex-2-en-1-yl)-3-methylpenta-2,4-dienoate The title compound was prepared according to the procedure of Compound 1b, substituting 5-thiazolecarboxaldehyde for 2-chloro-5-trifluoromethylbenzaldehyde.

Compound 35

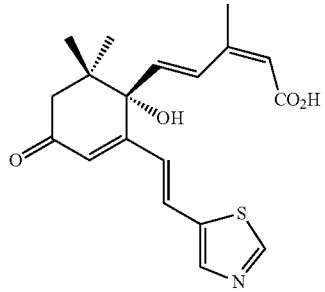

(2Z,4E)-5-((S)-1-hydroxy-6,6-dimethyl-4-oxo-2-((E)-2-(thiazol-5-yl)vinyl)cyclohex-2-en-1-yl)-3-methylpenta-2,4-dienoic acid The title compound was prepared according to the procedure of Compound 1, substituting Compound 35a for Compound 1b. $^1$HNMR (DMSO-$d_6$): δ12.11 (br s, 1H), 9.06 (s, 1H), 7.90 (s, 1H), 7.79 (d, 1H), 7.68 (d, 1H), 6.69 (d, 1H), 6.32 (s, 1H), 6.31 (d, 1H), 5.68 (s, 1H), 5.54 (s, 1H), 2.60 (d, 1H), 2.17 (d, 1H), 1.98 (d, 3H), 1.00 (s, 3H), 0.96 (s, 3H). MS (ESI−): m/e=358. Two-dimensional NMR experiments (COSY, NOESY, HSQC and HMBC) confirmed the structure.

Example 36

Compound 36a

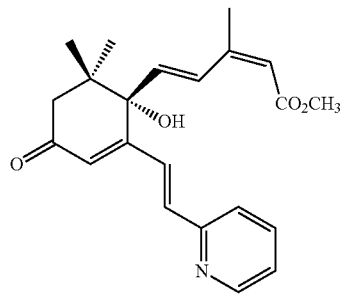

(2Z,4E)-methyl 5-((S)-1-hydroxy-6,6-dimethyl-4-oxo-2-((E)-2-(pyridin-2-yl)vinyl)cyclohex-2-en-1-yl)-3-methylpenta-2,4-dienoate The title compound was prepared according to the procedure of Compound 1b, substituting 2-pyridinecarboxaldehyde for 2-chloro-5-trifluoromethylbenzaldehyde.

Compound 36

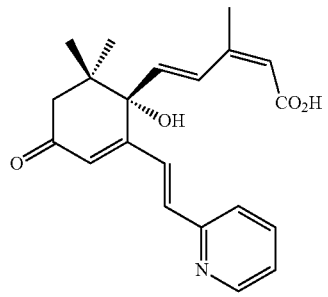

(2Z,4E)-5-((S)-1-hydroxy-6,6-dimethyl-4-oxo-2-((E)-2-(pyridin-2-yl)vinyl)cyclohex-2-en-1-yl)-3-methylpenta-2,4-dienoic acid The title compound was prepared according to the procedure of Compound 1, substituting Compound 36a for Compound 1b. ¹HNMR (CDCl₃): δ8.53 (d, 1H), 8.16 (d, 1H), 7.71 (dt, 1H), 7.52 (d, 1H), 7.36 (d, 1H), 7.27 (d, 1H), 7.23 (dd, 1H), 6.39 (s, 1H), 6.23 (d, 1H), 5.77 (s, 1H), 2.53-2.40 (d, 1H), 2.01 (d, 3H), 1.17 (s, 3H), 1.09 (s, 3H). MS (ESI−): m/e=352. Two-dimensional NMR experiments (COSY, NOESY, HSQC and HMBC) confirmed the structure.

Example 37

Compound 37a

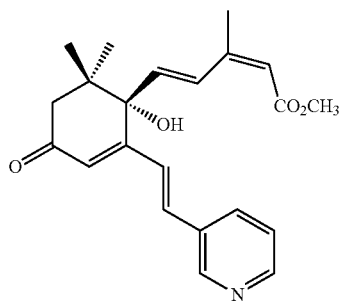

(2Z,4E)-methyl 5-((S)-1-hydroxy-6,6-dimethyl-4-oxo-2-((E)-2-(pyridin-3-yl)vinyl)cyclohex-2-en-1-yl)-3-methylpenta-2,4-dienoate The title compound was prepared according to the procedure of Compound 1b, substituting 3-pyridinecarboxaldehyde for 2-chloro-5-trifluoromethylbenzaldehyde.

Compound 37

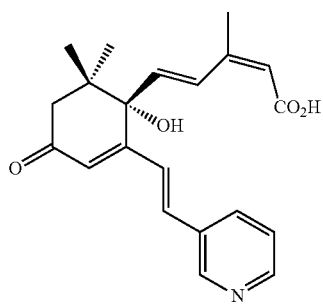

(2Z,4E)-5-((S)-1-hydroxy-6,6-dimethyl-4-oxo-2-((E)-2-(pyridin-3-yl)vinyl)cyclohex-2-en-1-yl)-3-methylpenta-2,4-dienoic acid The title compound was prepared according to the procedure of Compound 1, substituting Compound 37a for Compound 1b. ¹HNMR (DMSO-d₆): δ12.09 (br s, 1h), 8.69 (s, 1H), 8.49 (d, 1H), 7.94 (dt, 1H), 7.80 (d, 1H), 7.40 (d, 1H), 7.40 (dd, 1H), 7.03 (d, 1H), 6.34 (s, 1H), 6.33 (d, 1H), 5.68 (s, 1H), 5.50 (s, 1H), 2.60 (d, 1H), 2.17 (d, 1H), 1.98 (d, 3H), 1.01 (s, 3H), 0.97 (s, 3H). MS (ESI−): m/e=352. Two-dimensional NMR experiments (COSY, NOESY, HSQC and HMBC) confirmed the structure.

Example 38

Compound 38a

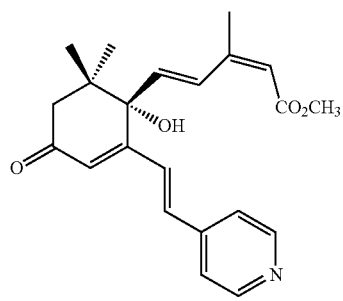

(2Z,4E)-methyl 5-((S)-1-hydroxy-6,6-dimethyl-4-oxo-2-((E)-2-(pyridin-4-yl)vinyl)cyclohex-2-en-1-yl)-3-methylpenta-2,4-dienoate The title compound was prepared according to the procedure of Compound 1b, substituting 4-pyridinecarboxaldehyde for 2-chloro-5-trifluoromethylbenzaldehyde.

Compound 38

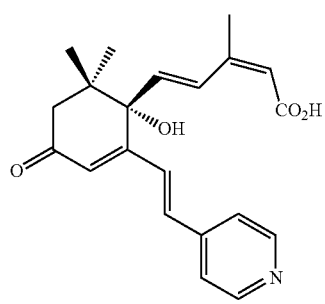

(2Z,4E)-5-((S)-1-hydroxy-6,6-dimethyl-4-oxo-2-((E)-2-(pyridin-4-yl)vinyl)cyclohex-2-en-1-yl)-3-methylpenta-2,4-dienoic acid The title compound was prepared according to the procedure of Compound 1, substituting Compound 38a for Compound 1b. ¹HNMR (DMSO-d₆): δ8.55 (d, 2H), 7.80 (d, 1H), 7.45 (dd, 2H), 7.35 (d, 1H), 7.16 (d, 1H), 6.37 (s, 1H), 6.33 (d, 1H), 5.68 (s, 1H), 5.55 (br s, 1H), 2.62 (d, 1H), 2.18 (d, 1H), 1.98 (d, 3H), 1.01 (s, 3H), 0.97 (s, 3H). MS (ESI−): m/e=352. Two-dimensional NMR experiments (COSY, NOESY, HSQC and HMBC) confirmed the structure.

Example 39

Seed Germination Assay for Testing Compounds 1 to 38

To determine whether the (S)-ABA derivatives of the present invention were effective antagonists, germination assays were performed with the model plant *Arabidopsis thaliana*. If the compounds are found to be antagonists, they may be useful to counter any undesirable side effects of (S)-ABA.

*Arabidopsis* seed was sterilized by shaking for five minutes in 200 proof ethanol, followed by shaking for five minutes in a 10% bleach solution. The seeds were then washed five times in sterile, distilled, de-ionized water and suspended in 0.1% phytoagar. The tubes containing the seeds were wrapped in aluminum foil and stratified at 4° C. for two days.

All compounds were tested at a concentration of 30 ppm in the presence or absence of 0.3 ppm (S)-ABA, in 24-well plates. For each compound, a 1000 ppm stock solution was prepared in distilled, deionized water containing 5% DMSO. The stock test solution (15 μL) was added to each well, plus or minus 1.5 μL of 100 ppm (S)-ABA in 5% DMSO. Appropriate amounts of distilled, de-ionized water was added to equalize volumes, and 450 μL of ½×Murashige and Skoog media containing 1.2% Bactoagar was then added to each well (final DMSO concentration was 0.5%). When the media solidified, ten to 15 sterile stratified *Arabidopsis* seeds were distributed into each well using a repeat pipettor. The plates were sealed with surgical tape and placed in a growth chamber running diurnal cycles of 12 hours of light at 24° C. and 12 hours of darkness at 19° C. The plates were scanned on days 3 through 14, and scored on day 14. The (S)-2'-vinyl-substituted ABA derivatives were scored on ability to promote germination in the presence of (S)-ABA. The results are summarized below in "Table 1: *Arabidopsis* seed germination promotion activity of 2'-vinyl-(S)-ABA derivatives."

TABLE 1

*Arabidopsis* seed germination promotion activity of 2'-vinyl-(S)-ABA derivatives

| Compound # | Rating |
| --- | --- |
| (S)-ABA | − |
| 1 | ++ |
| 2 | + |
| 3 | ++ |
| 4 | +++ |
| 5 | − |
| 6 | − |
| 7 | ++ |
| 8 | +++ |
| 9 | ++ |
| 10 | − |
| 11 | − |
| 12 | + |
| 13 | + |
| 14 | ++ |
| 15 | ++ |
| 16 | ++ |
| 17 | − |
| 18 | +++ |
| 19 | ++ |
| 20 | ++ |
| 21 | + |
| 22 | ++ |
| 23 | +++ |
| 24 | ++ |
| 25 | ++ |
| 26 | +++ |
| 27 | ++ |
| 28 | ++ |
| 29 | ++ |
| 30 | ++ |
| 31 | +++ |
| 32 | − |
| 33 | − |
| 34 | − |
| 35 | − |
| 36 | − |
| 37 | − |
| 38 | − |

Key:
−: Seeds germinated at approximately the same time as those treated with 0.3 ppm of (S)-ABA alone (i.e., treatment with the 2'-vinyl-(S)-ABA derivative showed no measurable effect in this assay configuration).
+: Seeds germinated 1 to 4 days earlier than those treated with 0.3 ppm of (S)-ABA alone.
++: Seeds germinated 5 to 7 days earlier than those treated with 0.3 ppm of (S)-ABA alone.
+++: Seeds germinated 8 to 10 days earlier than those treated with 0.3 ppm of (S)-ABA alone.

This biological assay is indicative of the overall antagonist nature of the derivatives compared to (S)-ABA.

In this assay, Applicant unexpectedly found that Compounds 4, 8, 18, 23, 26 and 31 were antagonists of (S)-ABA. Based on the known functions of (S)-ABA in plant physiology, these unexpected results imply that Compounds 4, 8, 18, 23, 26 and 31 will be effective at countering (S)-ABA action, including undesirable physiological effects of (S)-ABA treatment.

Example 40

Field Study for Breaking Grape Vine Dormancy

A small plot field study to test the effect of experimental compounds on release of, or breaking grape vine dormancy was conducted near Thermal, Calif. in January, 2016. The grapevines, Seedless 'Red Flame', had been pruned to 2-4 node spurs (shortened canes) prior to treatment. Aqueous treatment solutions were prepared with a test compound, an appropriate buffering agent, and a silicone-based nonionic surfactant at 0.25% (v/v). Each spur was thoroughly wetted with a 1% (w/v) solution, which was applied with a foam brush. Dormancy breaking was assessed periodically by examining bud break (initiation of growth) and subsequent shoot development. Compound 23, one of the most potent (S)-ABA antagonist as shown in Example 39 was chosen for this study. Both a control treatment (aqueous solution with surfactant) and a positive control treatment (the commercial standard for bud breaking, hydrogen cyanamide) were included in this study for comparison.

TABLE 2

Effect of Compound 23 on grape bud break and shoot development.

| Treatment | 31 days post-treatment Percent of Buds Broken | 48 days post-treatment Percent of Buds Broken | Shoot Length/Spur (cm)* |
| --- | --- | --- | --- |
| Control | 9.2 | 61.7 | 14.2 |
| Compound 23, 1% (v/v) | 16.7 | 76.7 | 22.2 |
| Hydrogen cyanamide, 1% (v/v) | 21.0 | 58.8 | 25.2 |

*Shoot length/spur includes the total length of all shoots present on spur

The application of compound 23 to dormant grape spurs significantly increased bud break. Unexpectedly, it was observed that at the 31 day post treatment assessment, treatment with compound 23 resulted in a significantly higher percentage of buds broken in comparison with the control (16.7% vs. 9.2%). Furthermore, it was unexpectedly observed that at 48 day post-treatment, treatment with compound 23 resulted in a higher percentage of broken buds than either the commercial standard or control (76.7% vs. 58.8% and 61.7%, respectively). The shoot length/spur from the broken buds for the vines treated with compound 23 was intermediate between the spurs treated with the control and hydrogen cyanamide. These results indicate that compound 23 is active in promoting breaking of woody plant dormancy.

Thus, these novel compounds as (S)-ABA antagonists, are effective for promoting germination in plant species with high seed dormancy and for promoting and synchronizing bud break in woody perennial plant species. These (S)-ABA antagonists may possess other agronomically valuable biological activities such as promoting plant growth, promoting plant heat stress tolerance, and inhibiting leaf yellowing, flower drop, and leaf drop in ornamental plant species.

The invention claimed is:

1. An enantiomerically pure compound of Formula I:

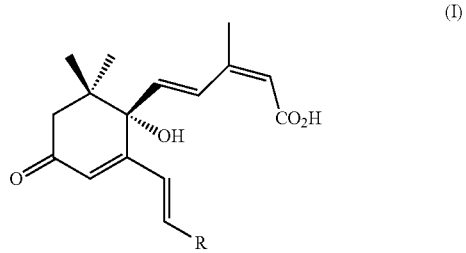

wherein R is selected from the group consisting of a substituted or unsubstituted benzene, naphthylene, a monocyclic or bicyclic heterocyclic aromatic ring, and salts thereof.

2. The compound of claim 1 wherein R is benzene.

3. The compound of claim 2 wherein the benzene ring is mono-, di-, tri-, tetra- or penta-substituted.

4. The compound of claim 3 wherein the substitution is selected from the group consisting of halogen, substituted or unsubstituted alkyl, cyano, alkoxy, nitro, sulfonyl, carbonyl, carboalkoxy and carbamoyl.

5. The compound of claim 4 wherein the substitution is an unsubstituted lower alkyl.

6. The compound of claim 5 wherein the unsubstituted lower alkyl is methyl.

7. The compound of claim 6 wherein the methyl substitution is 4-methyl-.

8. The compound of claim 2 wherein the benzene ring is mono-substituted with one halogen.

9. The compound of claim 8 wherein the halogen is selected from the group consisting of fluorine and chlorine.

10. The compound of claim 9 wherein the halogen substitution is 4-chloro-.

11. The compound of claim 3 wherein the benzene ring is disubstituted with two halogen substitutions.

12. The compound of claim 11 wherein the dihalogen substitutions are selected from the group consisting of difluoro-, dichloro-, and chloro-fluoro-.

13. The compound of claim 12 wherein the dihalogen substitution is 3-chloro-4-fluoro-.

14. The compound of claim 12 wherein the dihalogen substitution is 3,4-difluoro-.

15. The compound of claim 3 wherein the benzene ring is mono-substituted with dihalomethyl or trihalomethyl.

16. The compound of claim 15 wherein the mono-substitution is trihalomethyl.

17. The compound of claim 15 wherein the mono-substitution is trichloromethyl.

18. The compound of claim 15 wherein the mono-substitution is trifluoromethyl.

19. The compound of claim 18 wherein the trifluoromethyl substitution is 4-trifluoromethyl-.

20. The compound of claim 3 wherein the benzene ring is disubstituted with at least one halogen and at least one halomethyl selected from the group consisting of dihalomethyl and trihalomethyl.

21. The compound of claim 20 wherein the disubstitution is a halogen and a trihalomethyl group.

22. The compound of claim 21 wherein the halogen is fluorine and the trihalomethyl group is trifluoromethyl.

23. The compound of claim 22 wherein the fluorine substitution is 2-fluoro- and the trihalomethyl substitution is 3-trifluoromethyl-.

24. The compound of claim 1 wherein R is a monocyclic or bicyclic heterocyclic aromatic ring.

25. The compound of claim 24 wherein R is a pyridyl group.

26. The compound of claim 25 wherein the pyridyl is selected from the group consisting of 2-pyridyl, 3-pyridyl and 4-pyridyl.

27. The compound of claim 24 wherein R is a furyl group.

28. The compound of claim 24 wherein R is a thiazolyl group.

29. A process of making the compounds of claim 1 comprising:
   a. reacting (S)-abscisic acid with an alkylating agent and a carbonate base in a solvent to form an ester;
   b. treating the compound resulting from Step a with a base and an aromatic aldehyde or a heteroaromatic aldehyde in a solvent to form an olefin via the 7'-methyl group of (S)-ABA; and
   c. treating the compound resulting from Step b with a base in water or a mixture of water and an organic solvent.

30. A method of regulating plant growth comprising applying an effective amount of at least one of the compounds of claim 1 to a plant in need of growth regulation.

* * * * *